US008716258B2

(12) United States Patent
Olson et al.

(10) Patent No.: US 8,716,258 B2
(45) Date of Patent: May 6, 2014

(54) REGULATION OF METABOLISM BY MIR-378

(75) Inventors: Eric N. Olson, Dallas, TX (US);
Michele Carrer, Dallas, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/702,033

(22) PCT Filed: Jun. 6, 2011

(86) PCT No.: PCT/US2011/039308
§ 371 (c)(1),
(2), (4) Date: Feb. 27, 2013

(87) PCT Pub. No.: WO2011/153542
PCT Pub. Date: Dec. 8, 2011

(65) Prior Publication Data
US 2013/0150427 A1   Jun. 13, 2013

Related U.S. Application Data

(60) Provisional application No. 61/351,683, filed on Jun. 4, 2010.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC ........................................ 514/44 A; 536/24.5

(58) Field of Classification Search
USPC ............................................ 514/44; 536/24.5
See application file for complete search history.

(56) References Cited

U.S. PATENT DOCUMENTS

| 7,928,219 | B2 | 4/2011 | McSwiggen et al. |
| 8,110,674 | B2 | 2/2012 | Manoharan et al. |
| 8,188,059 | B2 | 5/2012 | Bhanot et al. |
| 8,222,221 | B2 | 7/2012 | Corey et al. |

(Continued)

FOREIGN PATENT DOCUMENTS

| EP | 2446929 A1 | 5/2012 |
| WO | WO 2005/099770 A2 | 10/2005 |

(Continued)

OTHER PUBLICATIONS

Carrer et al. (Proceedings of the National Academy of Science, 2012 vol. 109, No. 38:15330-15335).*

(Continued)

*Primary Examiner* — Terra Cotta Gibbs
(74) *Attorney, Agent, or Firm* — Cooley LLP

(57) ABSTRACT

The present invention provides a method of regulating fatty acid metabolism in a cell by contacting the cell with a modulator of miR-378 and/or miR-378* activity or expression. The present invention also provides a method of treating or preventing a metabolic disorder, such as obesity, diabetes, or metabolic syndrome, in a subject by administering to the subject an inhibitor of miR-378 and/or miR-378* expression or activity. Methods of treating or preventing pathologic cardiac hypertrophy, cardiac remodeling, myocardial infarction, or heart failure in a subject by inhibiting the expression or activity of miR-378 and/or miR-378* in a subject are also disclosed.

32 Claims, 24 Drawing Sheets

(56) References Cited

U.S. PATENT DOCUMENTS

| | | |
|---|---|---|
| 8,236,939 B2 | 8/2012 | Bentwich et al. |
| 2008/0176766 A1 | 7/2008 | Brown et al. |
| 2009/0043082 A1 | 2/2009 | Stoffel et al. |
| 2009/0143326 A1 | 6/2009 | Obad et al. |
| 2009/0176723 A1 | 7/2009 | Brown et al. |
| 2009/0286753 A1 | 11/2009 | Kauppinen et al. |
| 2010/0004320 A1 | 1/2010 | Elmen et al. |
| 2010/0021914 A1 | 1/2010 | Møller |
| 2010/0088775 A1 | 4/2010 | Khew-Goodall et al. |
| 2010/0173288 A1 | 7/2010 | Zhang et al. |
| 2010/0197772 A1 | 8/2010 | Califano et al. |
| 2010/0256223 A1 | 10/2010 | Møller |
| 2010/0273255 A1 | 10/2010 | Tuschl et al. |
| 2010/0279292 A1 | 11/2010 | Marsh et al. |
| 2010/0292310 A1 | 11/2010 | Kelley et al. |
| 2010/0298410 A1 | 11/2010 | Obad et al. |
| 2010/0305188 A1 | 12/2010 | Nakano et al. |
| 2011/0104236 A1 | 5/2011 | Dana et al. |
| 2011/0152352 A1 | 6/2011 | Hata et al. |
| 2011/0160285 A1 | 6/2011 | Anderson et al. |
| 2012/0077265 A1 | 3/2012 | Stoffel et al. |
| 2012/0083596 A1 | 4/2012 | Elmen et al. |
| 2012/0172416 A1 | 7/2012 | Velin et al. |

FOREIGN PATENT DOCUMENTS

| | | |
|---|---|---|
| WO | WO 2006/137941 A2 | 12/2006 |
| WO | WO 2007/042899 A2 | 4/2007 |
| WO | WO 2007/090073 A2 | 8/2007 |
| WO | WO 2007/112754 A2 | 10/2007 |
| WO | WO 2008/154098 A2 | 12/2008 |
| WO | WO 2009/058907 A2 | 5/2009 |
| WO | WO 2009/114681 A2 | 9/2009 |
| WO | WO 2009/149182 A1 | 12/2009 |
| WO | WO 2009/151600 A2 | 12/2009 |
| WO | WO 2010/003420 A2 | 11/2010 |
| WO | WO 2011/029903 A1 | 3/2011 |
| WO | WO 2011/028550 A1 | 10/2011 |
| WO | WO 2011/154553 A2 | 12/2011 |
| WO | WO 2012/145374 A1 | 10/2012 |

OTHER PUBLICATIONS

Kuwabara et al., "MicroRNA-378, Which Exists Intronic Lesion of PGC-1beta, Deteriorate Cardiomyocyte Survival Under Oxidative Stress," Circulation, vol. 120: S735, Abstract 3025, 2009.

Young, "International Search Report and Written Opinion," 9 pages, International Application No. PCT/US2011/039308, United States Patent Office, mailed Jan. 5, 2012.

Prasad et al., "Association analysis of ADPRT1, AKRIB1, RAGE, GFPT2 and PAI-1 gene polymorphisms with chronic renal insufficiency among Asian Indians with type-2 diabetes," BMC Medical Genetics, vol. 11:52-60, 2010.

Gerin et al., "Roles for miRNA-378/378* in adipocyte gene expression and lipogenesis," Am J Physiol Endocrinol Metab., vol. 299(2): E198-E206, 2010.

Jin et al., "Characterization of microRNA expression in bovine adipose tissues: a potential regulatory mechanism of subcutaneous adipose tissue development," BMC Molecular Biology, vol. 11:29-36, 2010.

\* cited by examiner

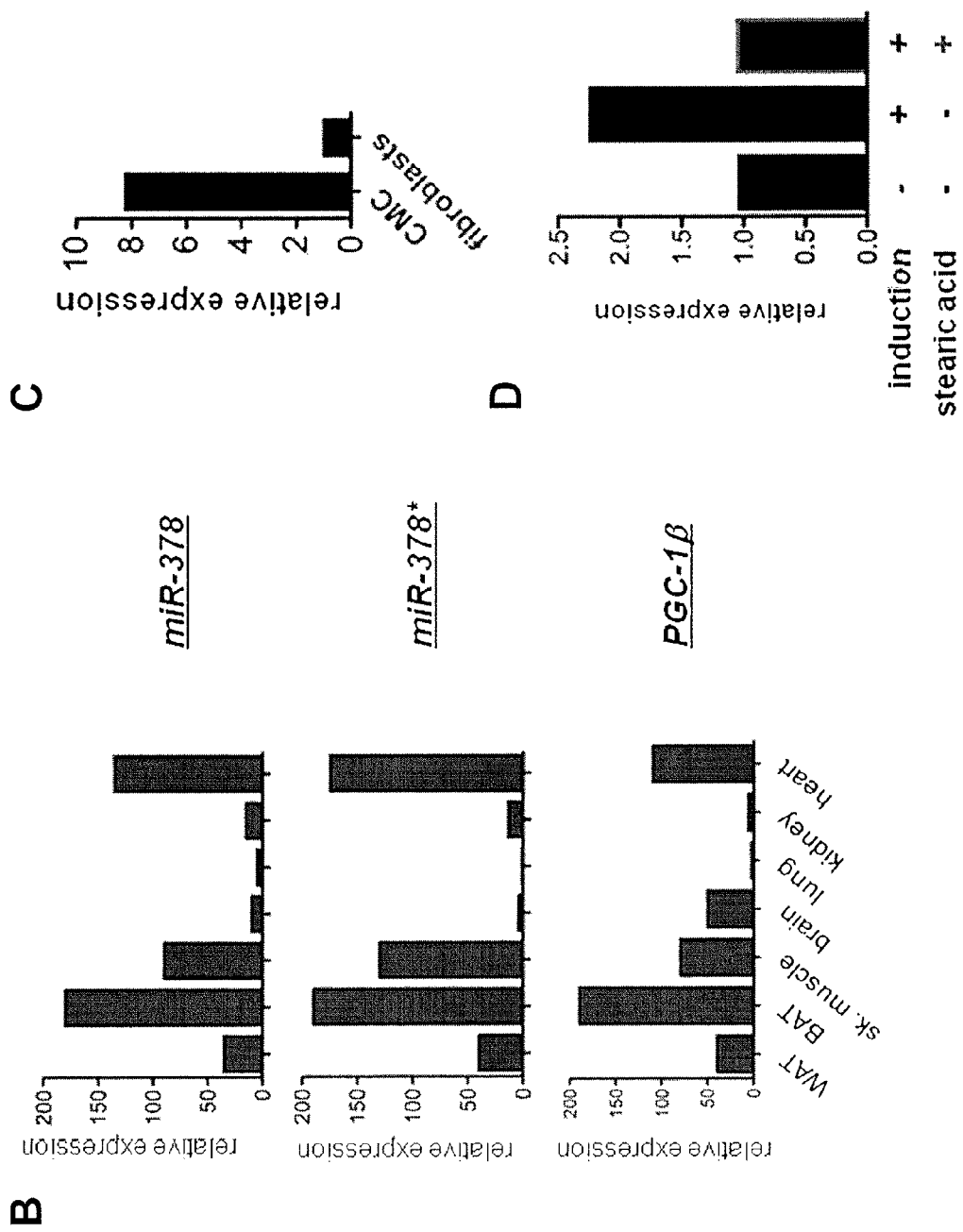
FIGURE 1B-D

FIGURE 2A-B
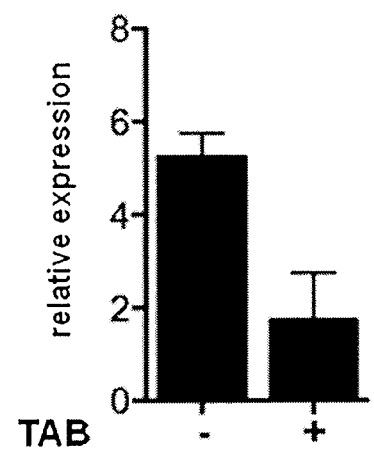
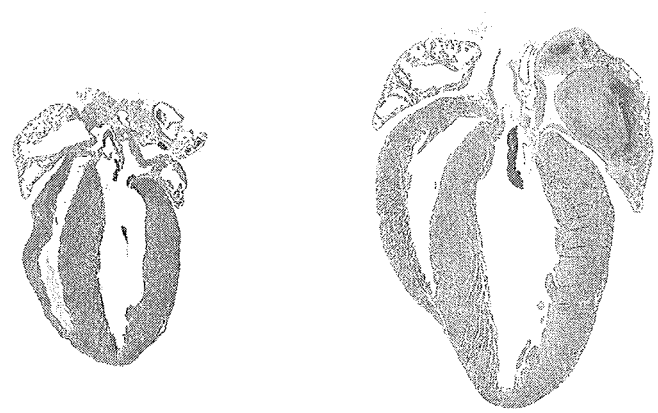
Wild-type   miR-378 transgenic

FIGURE 8B-C
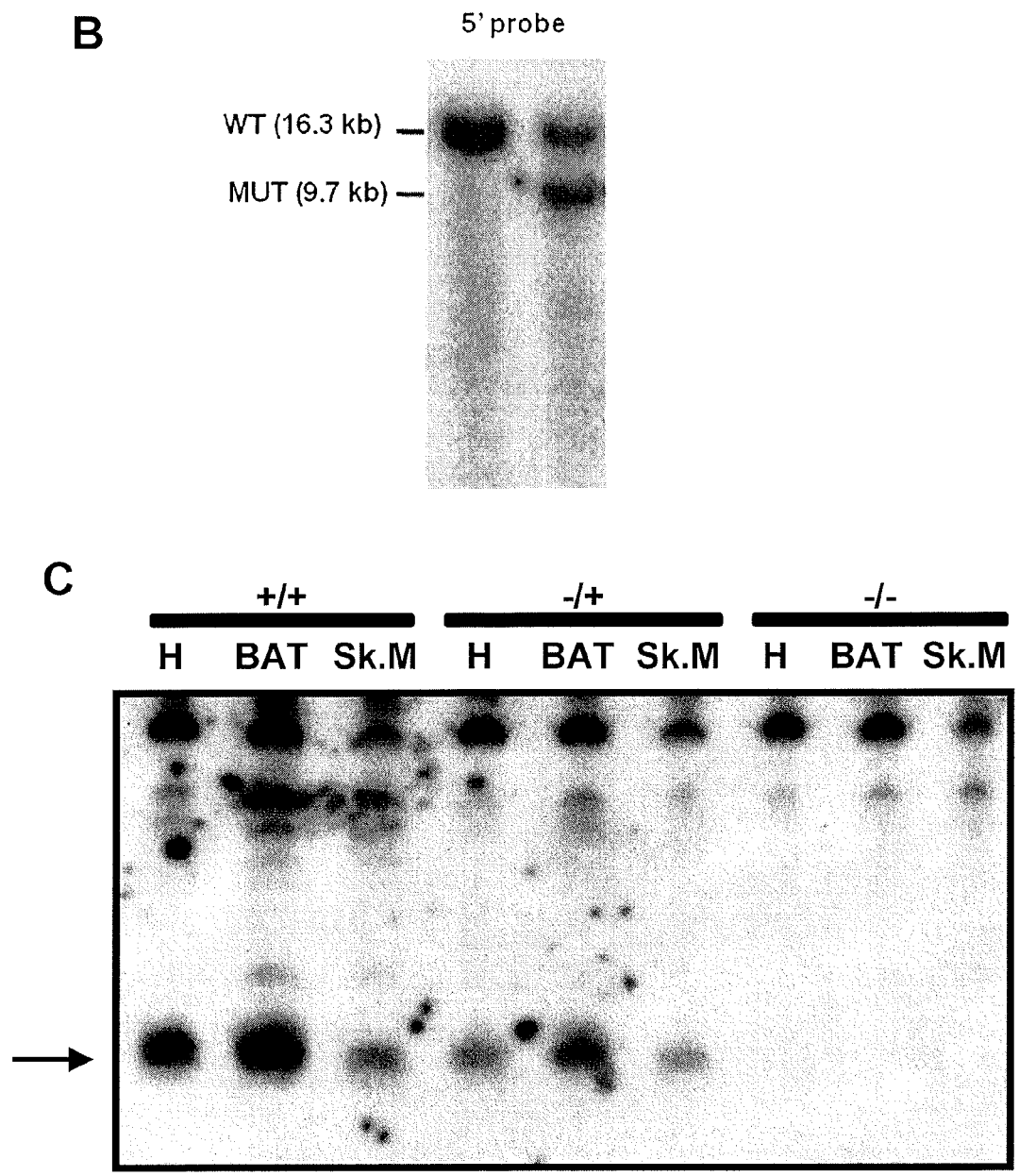

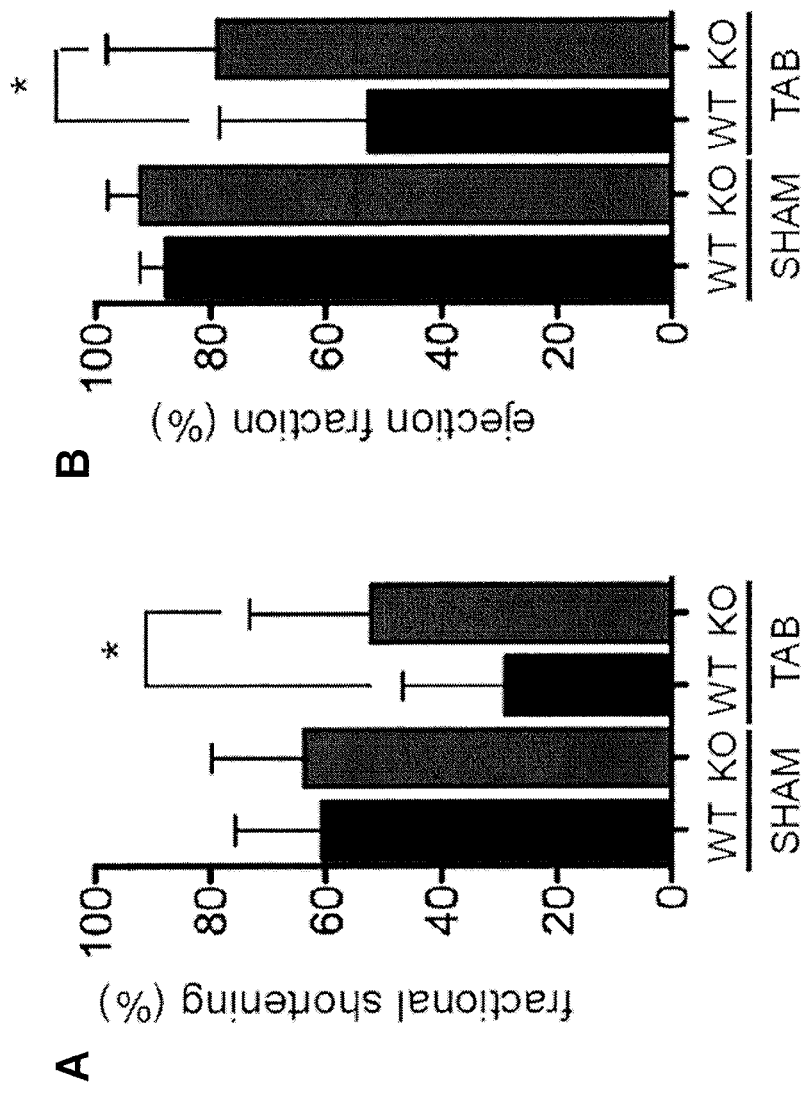
FIGURE 10A-B

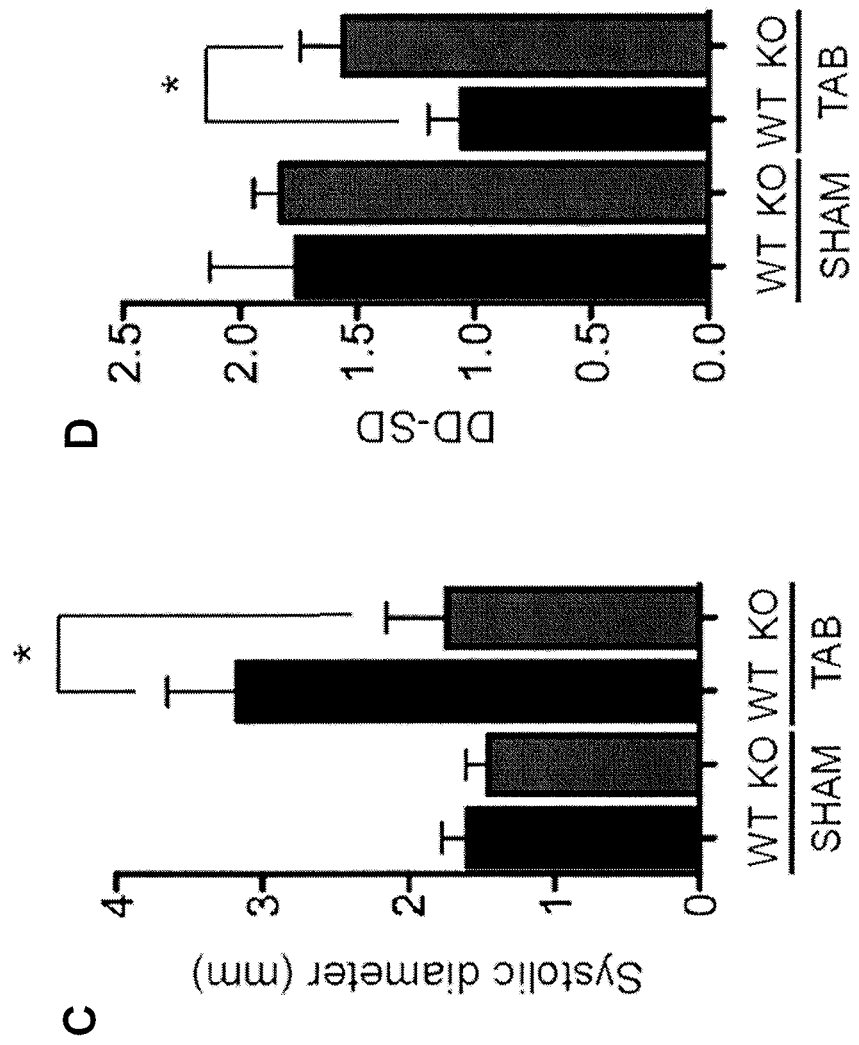
FIGURE 10C-D

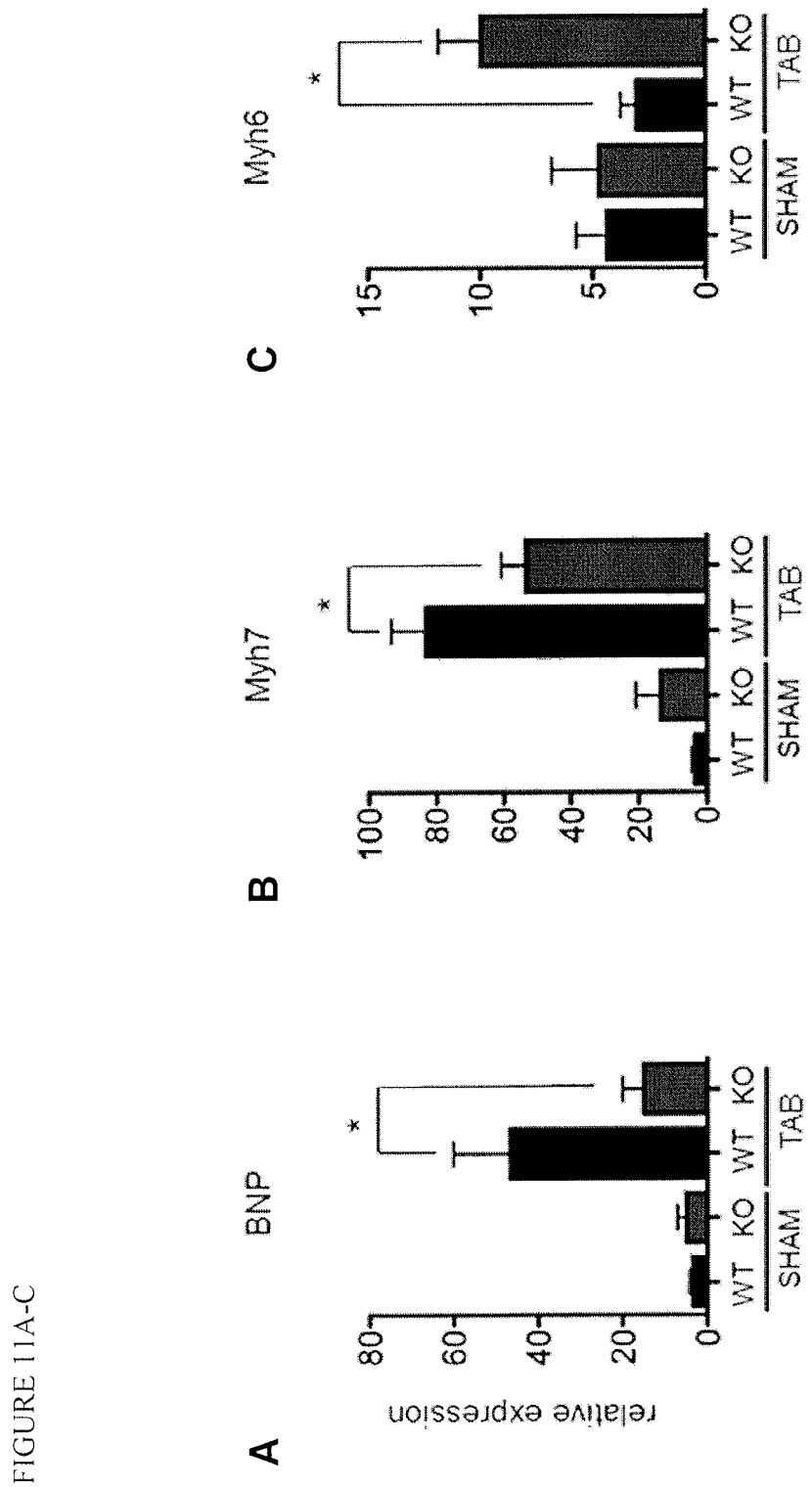
FIGURE 11A-C

FIGURE 13A-B

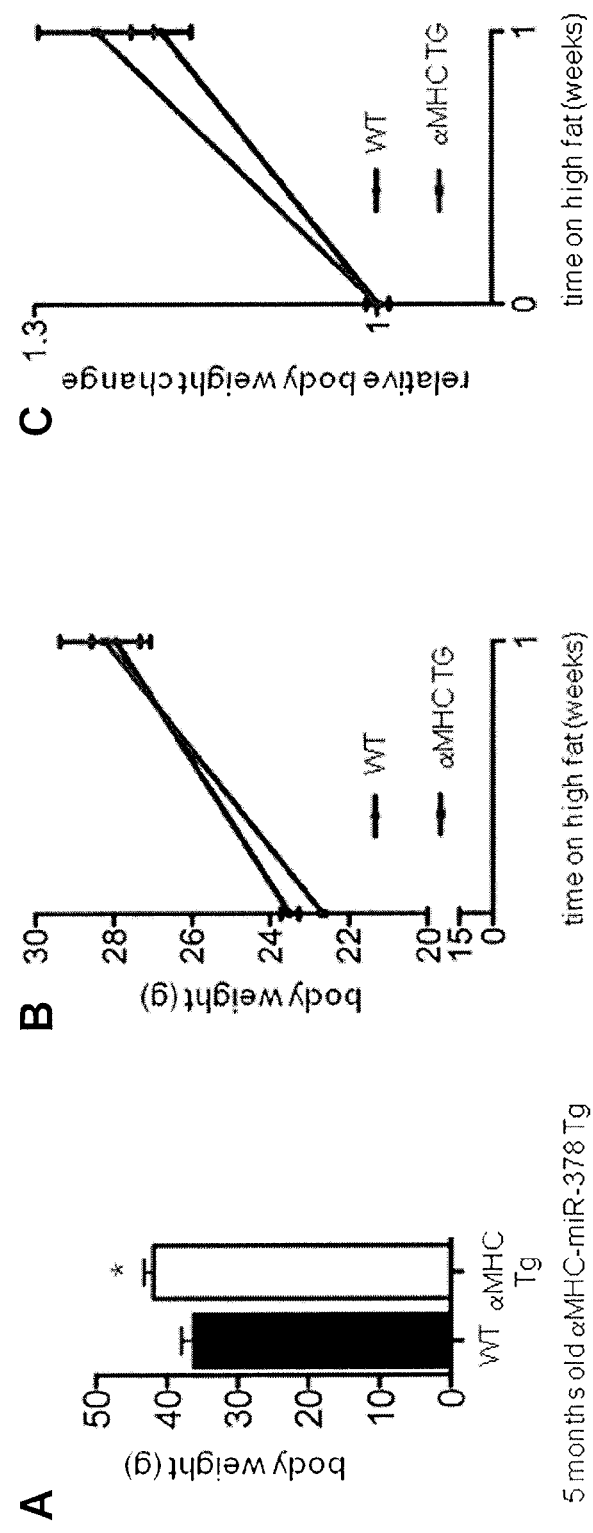
FIGURE 17A-C

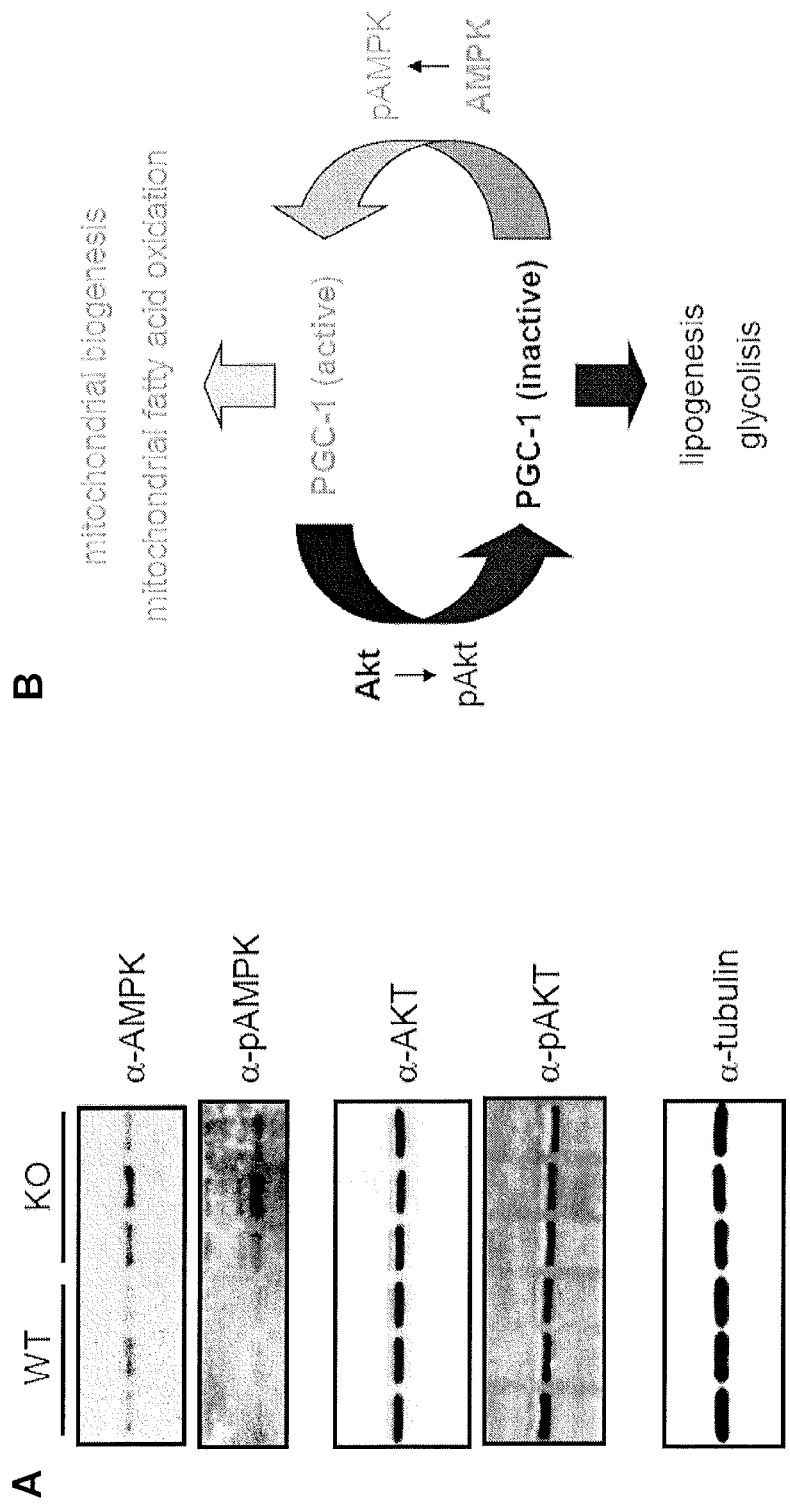
FIGURE 18A-B

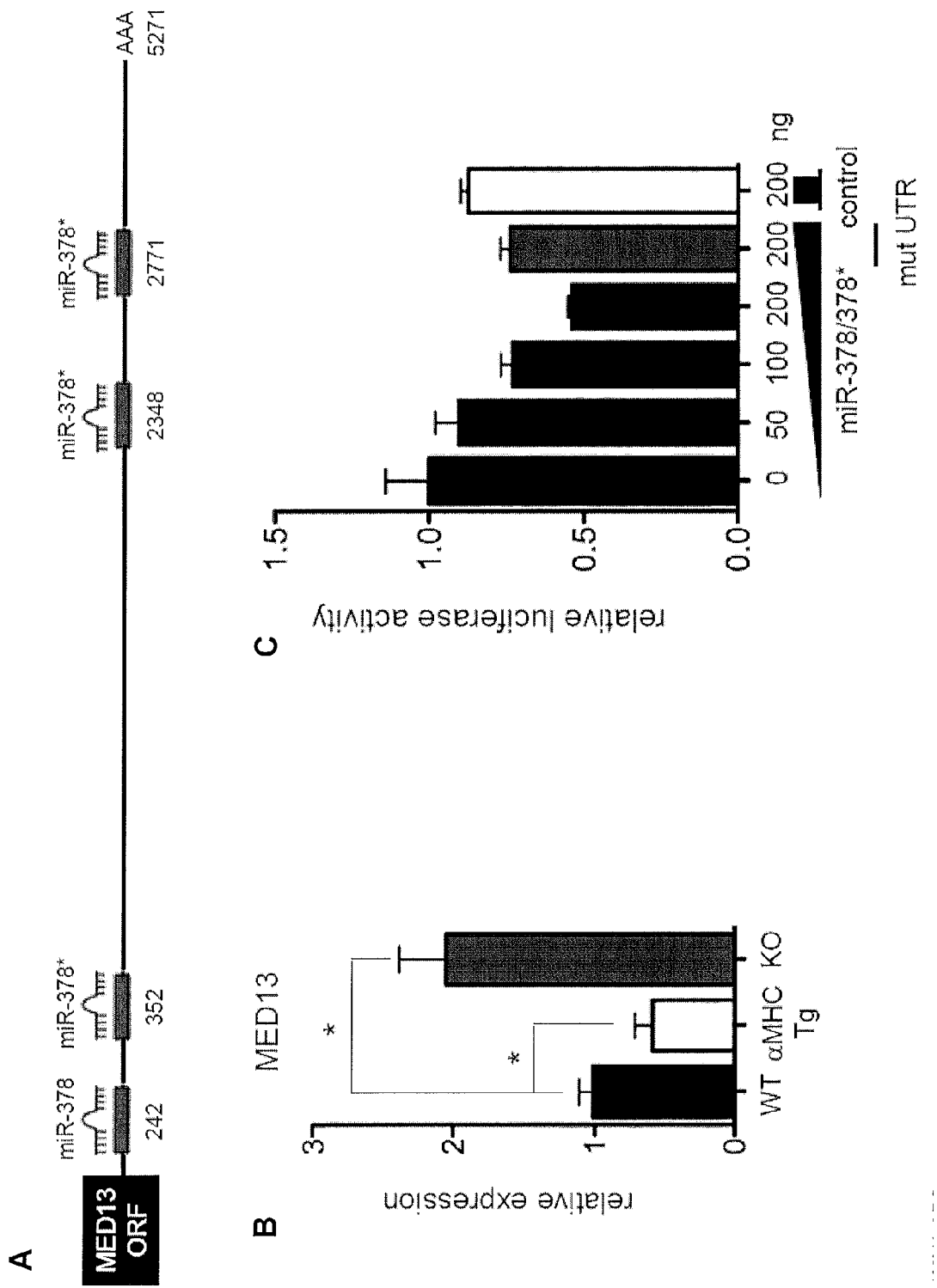
FIGURE 19A-C

REGULATION OF METABOLISM BY MIR-378

CROSS-REFERENCE TO RELATED APPLICATIONS

This application is a national stage application of International Application No. PCT/US2011/039308, filed Jun. 6, 2011, which claims priority to U.S. Provisional Application Ser. No. 61/351,683, filed Jun. 4, 2010, all of which are hereby incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_022_01WO_SeqList_ST25.txt, date recorded: Jun. 6, 2011, file size 5 kilobytes).

FIELD OF THE INVENTION

The present invention relates to the treatment and prevention of cardiac and metabolic disorders by administering agents that modulate the activity or expression of a microRNA (miRNA). In particular, the invention provides a method for treating or preventing cardiac and metabolic disorders by inhibiting the expression or activity of miR-378/miR-378* in cells of a subject. In addition, the invention provides a method for regulating fatty acid metabolism in a cell by contacting the cell with a modulator of miR-378/miR-378* expression or activity.

BACKGROUND OF THE INVENTION

Heart disease and its manifestations, including coronary artery disease, myocardial infarction, congestive heart failure and cardiac hypertrophy, clearly present a major health risk in the United States today. The cost to diagnose, treat and support patients suffering from these diseases is well into the billions of dollars. Two particularly severe manifestations of heart disease are myocardial infarction and cardiac hypertrophy.

Myocardial infarction, commonly known as a heart attack, is caused by a sudden and sustained lack of blood flow to the heart tissue, which is usually the result of a narrowing or occlusion of a coronary artery. Without adequate blood supply, the tissue becomes ischemic, leading to the death of cardiomyocytes (e.g. heart muscle cells) and vascular structures. The necrotic tissue resulting from the death of the cardiomyocytes is generally replaced by scar tissue, which is not contractile, fails to contribute to cardiac function, and often plays a detrimental role in heart function by expanding during cardiac contraction, or by increasing the size and effective radius of the ventricle, for example, becoming hypertrophic.

Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to dilated cardiomyopathy (DCM), heart failure, and sudden death. In the United States, approximately half a million individuals are diagnosed with heart failure each year, with a mortality rate approaching 50%.

Numerous signaling pathways, especially those involving aberrant calcium signaling, drive cardiac hypertrophy and pathological remodeling (Heineke & Molkentin, 2006). Hypertrophic growth in response to stress involves different signaling pathways and gene expression patterns than physiological hypertrophy, which occurs in response to exercise. Stress-mediated myocardial hypertrophy is a complex phenomenon associated with numerous adverse consequences with distinct molecular and histological characteristics causing the heart to fibrose, dilate and decompensate which, through cardiomyocyte degeneration and death, often culminates in heart failure. As such, there has been intense interest in deciphering the underlying molecular mechanisms and in discovering novel therapeutic targets for suppressing adverse cardiac growth and ultimately failure. Understanding these mechanisms is essential to the design of new therapies to treat cardiac hypertrophy and heart failure.

Metabolic syndrome is a combination of medical disorders that increase the risk of developing cardiovascular disease and diabetes. It affects one in five people, and prevalence increases with age. Some studies estimate the prevalence in the U.S. to be up to 25% of the population (Ford et al. (2002) JAMA, Vol. 287:356-359). People afflicted with metabolic syndrome are generally obese, sedentary, and have a certain degree of insulin resistance. Obesity is a leading preventable cause of death worldwide, with increasing prevalence in adults and children, and authorities view it as one of the most serious public health problems of the 21st century (Barness et al. (2007) Am. J. Med. Genet. A, Vol. 143A: 3016-34). Obesity can lead to reduced life expectancy and increased health problems, including heart disease, type 2 diabetes, sleep apnea, certain types of cancer, and osteoarthritis. Current therapies for metabolic syndrome and obesity focus on dieting and exercise with very few effective pharmaceutical interventions available. The effectiveness of diet and exercise in improving these conditions varies greatly among patients and tends to provide only a moderate degree of weight loss and improvement in symptoms. Therefore, there is a need for novel therapeutic approaches to treat metabolic disorders and prevent the subsequent development of cardiovascular disease and heart failure.

MicroRNAs have recently been implicated in a number of biological processes including regulation of developmental timing, apoptosis, fat metabolism, and hematopoietic cell differentiation among others. MicroRNAs (miRNAs) are small, non-protein coding RNAs of about 18 to about 25 nucleotides in length that are derived from individual miRNA genes, from introns of protein coding genes, or from polycistronic transcripts that often encode multiple, closely related miRNAs. See review by Carrington et al. (*Science*, Vol. 301(5631):336-338, 2003). MiRNAs act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al. (2006) *Cellular & Molecular Immunology*, Vol. 3:411-419) and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

Recently, signature expression patterns of miRNAs associated with pathological cardiac hypertrophy, heart failure and myocardial infarction in humans and mouse models of heart disease have been identified (van Rooij et al (2006) Proc. Natl. Acad. Sci., Vol. 103(48):18255-60; van Rooij et al., (2007) Science, Vol. 316: 575-579). Gain- and loss-of-function studies in mice have revealed profound and unexpected functions for these miRNAs in numerous facets of cardiac biology, including the control of myocyte growth, contractility, energy metabolism, fibrosis, and angiogenesis, providing glimpses of new regulatory mechanisms and potential therapeutic targets for heart disease. Remarkably, knockout mice lacking disease-inducing miRNAs are normal, but display aberrant responses to cardiac stress, suggesting the dedication of these miRNAs to disease-related processes rather than tissue homeostasis, and pointing to their potential as therapeutic targets. Thus, miRNAs represent potential novel therapeutic targets for the development of treatments for a variety of diseases, including cardiovascular diseases, obesity, diabetes, and other metabolic disorders.

SUMMARY OF THE INVENTION

The present invention is based, in part, on the discovery that the expression of miR-378 is down-regulated in heart tissue following pressure overload and that overexpression of miR-378 in a cardiac-specific manner exacerbates the cardiac hypertrophic response induced by stress. Overexpression of miR-378/miR-378* in skeletal muscle produces increased body weight resulting from increased mass of epididymal fat pads due to adipocyte hypertrophy and possibly adipocyte hyperplasia. Thus, the inventors have surprisingly found that miR-378/miR-378* regulates metabolic processes in different tissues, including cardiac and adipose tissue. Accordingly, the present invention provides methods of treating or preventing cardiovascular disease and other metabolic disorders, such as obesity and diabetes, by modulating the expression or activity of miR-378 and/or miR-378* in cells in a subject in need thereof.

In one embodiment, the present invention provides a method of treating or preventing pathologic cardiac hypertrophy, cardiac remodeling, myocardial infarction, or heart failure in a subject in need thereof comprising administering to the subject an inhibitor of miR-378 and/or miR-378*. In certain embodiments, the expression or activity of miR-378 and/or miR-378* is reduced in the heart cells of the subject following administration. In other embodiments, the stress-induced metabolic shift from oxidative to glycolytic metabolism is prevented or reduced in heart cells of the subject following administration of the miR-378 and/or miR-378* inhibitor.

The present invention also includes a method of treating or preventing a metabolic disorder in a subject in need thereof. In one embodiment, the method comprises administering to the subject an inhibitor of miR-378 and/or miR-378*, wherein the expression or activity of miR-378 and/or miR-378* is reduced in the cells of the subject following administration. The metabolic disorder to be treated can include metabolic syndrome, obesity, diabetes mellitus, diabetic nephropathy, insulin resistance, atherosclerosis, a lipid storage disorder, a glycogen storage disease, medium-chain acyl-coenzyme A dehydrogenase deficiency, lipid oxidation, or aberrant glucose uptake and/or utilization. Secondary diseases or conditions resulting from these metabolic disorders can also be prevented or treated with the methods of the invention. For example, in one embodiment, the invention provides a method of preventing or treating secondary diseases or disorders resulting from obesity, such as sleep apnea, cancer, and osteoarthritis, by administering an inhibitor of miR-378 and/or miR-378*.

The miR-378 and miR-378* inhibitors suitable for use in the methods of the invention can be antisense oligonucleotides. In one embodiment, the antisense oligonucleotide comprises a sequence that is at least partially complementary to a mature sequence of miR-378 or miR-378*. In certain embodiments, the antisense oligonucleotides comprise one or more sugar or backbone modifications, such as locked nucleic acids, bicyclic nucleosides, phosphonoformates, 2' O-alkyl modifications, and phosphorothioate linkages. In other embodiments, the miR-378 or miR-378* inhibitor is an antisense oligonucleotide of about 7 to about 18 nucleotides in length.

In another embodiment, the present invention provides a method of regulating fatty acid metabolism in a cell comprising contacting the cell with a modulator of miR-378 and/or miR-378* expression or activity. The modulator can be an inhibitor or agonist of miR-378 and/or miR-378* expression or activity. In certain embodiments, fatty acid metabolism is increased in the cell following contact with a miR-378 and/or miR-378* inhibitor as compared to a cell not exposed to the inhibitor. In other embodiments, fatty acid metabolism is decreased in the cell following contact with the miR-378 and/or miR-378* agonist as compared to a cell not exposed to the agonist. The cell may be in vitro or in vivo. In some embodiments, the cell is a cardiomyocyte, a skeletal muscle cell, a preadipocyte, an adipocyte, a hepatocyte, or a pancreatic cell.

The present invention also includes a method of regulating cardiac metabolism. In one embodiment, the method comprises contacting a cardiomyocyte with a modulator of miR-378 and/or miR-378* expression or activity. The cardiomyocyte can be in vitro or in vivo. In another embodiment, carbohydrate metabolism is reduced in the cardiomyocyte following contact with a miR-378 and/or miR-378* inhibitor. In still another embodiment, fatty acid metabolism is increased in the cardiomyocyte following contact with a miR-378 and/or miR-378* inhibitor.

The present invention encompasses pharmaceutical compositions comprising the miR-378 and miR-378* inhibitors and agonists described herein and a pharmaceutically acceptable carrier. In one embodiment, the pharmaceutical composition comprises an inhibitor of miR-378 and/or miR-378* and a pharmaceutically acceptable carrier, wherein the inhibitor is an antisense oligonucleotide. In certain embodiments, the antisense oligonucleotide comprises at least one sugar and/or backbone modification. In other embodiments, the antisense oligonucleotide is about 7 to about 18 nucleotides in length.

BRIEF DESCRIPTION OF THE DRAWINGS

FIG. 2. A. MiR-378 is down-regulated in the heart upon thoracic aortic banding (TAB) compared to untreated heart (sham controls) as shown by quantitative realtime PCR. B. Myocardial overexpression of miR-378 induces an exacerbated hypertrophic response upon TAB.

FIG. 10. Echocardiography was performed in wild-type (WT) and miR-378 knockout (KO) mice 21 days after thoracic aortic banding (TAB) to determine fractional shortening (A), ejection fraction (B), systolic diameter (C), and diastolic-systolic diameter (DD-SD)(D).

FIG. 11. Expression of stress-induced genes, BNP (A), Myh7 (B), and Myh6 (C), in heart tissue of wild-type (WT) and miR-378 knockout (KO) mice following thoracic aortic banding (TAB) as assessed by real time PCR.

FIG. 17. Mice overexpressing miR-378/miR-378* in heart tissue under the control of the alpha-myosin heavy chain promoter (α-MHC TG) have increased body weight (A) and exhibit a greater increase in body weight on a high fat diet (B and C) as compared to wild-type (WT) littermates.

FIG. 18. A. Western blot analysis of brown adipose tissue isolated from wild-type (WT) and miR-378 knockout (KO) six hours after fasting. Blots were probed with antibodies specific for the phosphorylated and non-phosphorylated forms of AMPK and AKT. Alpha-tubulin was used as a control. B. Schematic showing regulation of metabolism by AMPK and AKT signaling pathways.

FIG. 19. A. Schematic of 3' UTR of MED13 depicting the putative binding sites for miR-378/miR-378*. B. Expression levels of MED13 in wild-type (WT), miR-378 transgenics overexpressing miR-378 under the control of the αMHC promoter (αMHC Tg), and miR-378 knockout (KO) animals. C. COS1 cells were transfected with a MED13 3'UTR luciferase construct, along with expression plasmids for miR-378 and a control miRNA. Values shown are fold-change in luciferase expression (±SEM) compared to the reporter alone.

DETAILED DESCRIPTION OF THE INVENTION

Figure 1A:
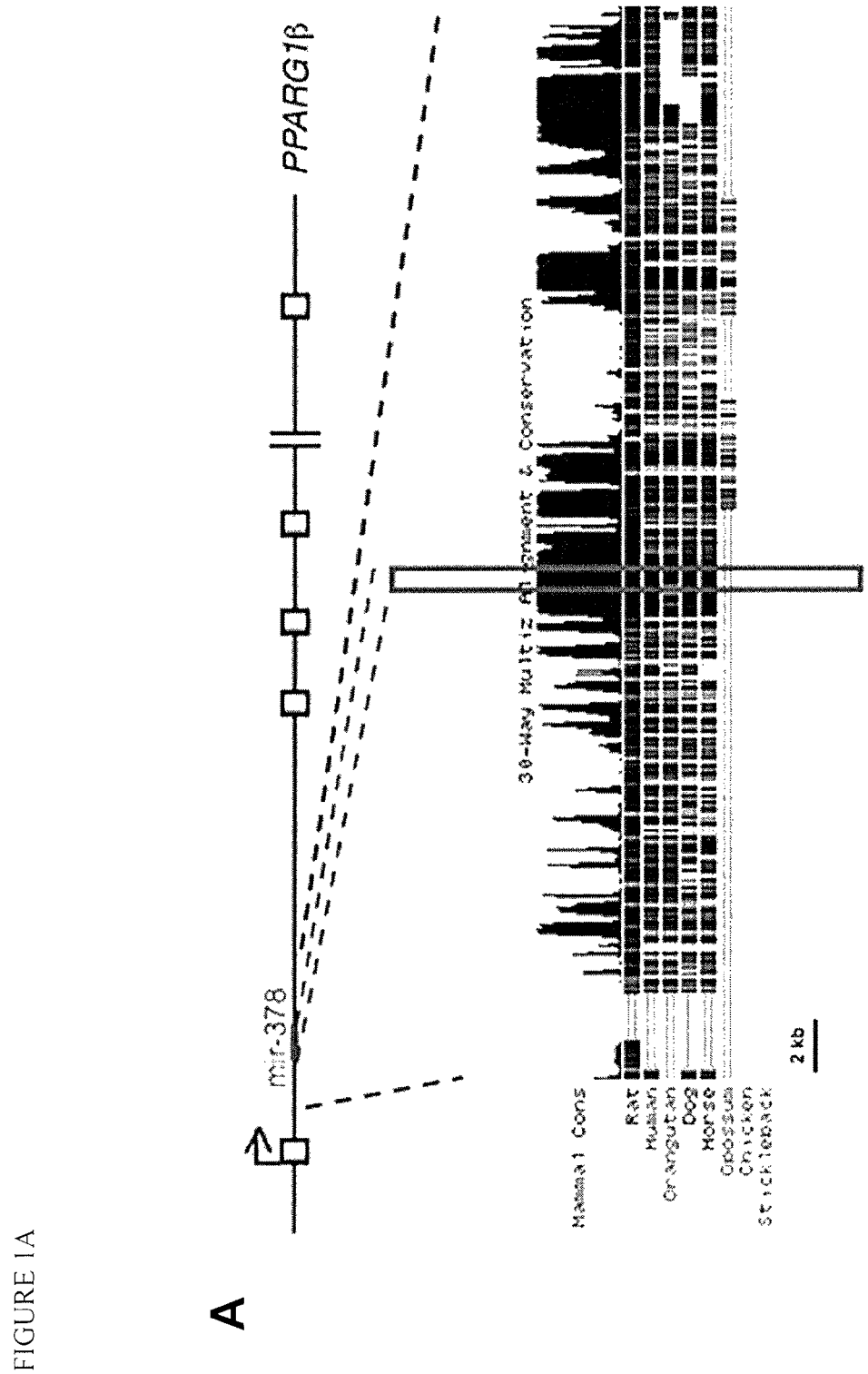
FIG. 1. A. Genomic location of miR-378 within the host gene PPARGC1β (top). UCSC Genome Browser illustration of the conservation of the genomic region surrounding miR-378 (bottom). B. Quantitative real-time PCR analysis shows that miR-378, miR-378*, and PPARGC1β (PGC-1β), the host gene of miR-378/miR-378* are specifically expressed in heart, skeletal muscle and brown adipose tissue. C. miR-378 is more highly expressed in cardiomyocytes than in cardiac fibroblasts. D. miR-378 expression is reduced upon treatment of HIB1B cells with stearic acid. E. miR-378 and PPARGC1β (PGC-1β) expression during induction of adipocyte differentiation. CMC: cardiomyocytes, BAT: brown adipose tissue, WAT: white adipose tissue.

Chronic and acute stress to the heart results in a pathological remodeling response accompanied by hypertrophy, fibrosis, myocyte apoptosis and eventual death from pump failure and arrhythmias. While classical pharmacological treatment strategies (e.g. beta-blockers and ACE-inhibitors) can prolong survival in heart failure patients, these therapies are ultimately ineffective in preventing progression of the disease, underscoring the need for new mechanistic insights and therapeutic approaches.

Heart failure is a progressive long-term disease that affects an estimated 5.7 million Americans with increasing associated healthcare costs (Lloyd-Jones et al. (2009) Circulation, Vol. 119:21-181). MiRNAs have recently emerged as important molecular components in hypertrophy and remodeling in the heart, thus representing a promising target in the prevention and treatment of heart disease. Because individual miRNAs often regulate the expression of multiple target genes with related functions, modulating the expression of a single miRNA can, in principle, influence an entire gene network and thereby modify complex disease phenotypes.

The present invention is based, in part, on the discovery of a miRNA that is highly expressed in the mitochondrial-rich tissues of the heart, skeletal muscle, and brown adipose and is regulated in various cardiac disease states. In particular, the inventors have surprisingly discovered that miR-378 and its counterpart minor sequence, miR-378*, are regulators of global metabolism. MiR-378 plays a role in the stress-induced cardiac hypertrophic response through the regulation of cardiac metabolism and is implicated in glucose utilization and fatty acid metabolism in skeletal muscle. Accordingly, the present invention provides a method of preventing or treating various cardiac and metabolic disorders in a subject by inhibiting the expression or activity of miR-378 and/or miR-378* in cells of the subject.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human.

MiR-378 is encoded on murine chromosome 18, within the first intron of the Peroxisome proliferator-activated receptor gamma coactivator 1-beta (PPARGC1β) gene. In humans, miR-378 (previously named miR-422b) is expressed from the first intron of the PPARGC1β gene on chromosome 5. The pre-miRNA sequence for miR-378 is processed into a mature sequence and a star (i.e. minor) sequence. The star sequence is processed from the other arm of the stem loop structure. The pre-miRNA (e.g. stem-loop sequences), mature, and star sequences for mouse and human miR-378 are given below:

```
Human mature miR-378
                                        (SEQ ID NO: 1)
5'- ACUGGACUUG GAGUCAGAAG G-3'

Human miR-378*
                                        (SEQ ID NO: 2)
5'- CUCCUGACUC CAGGUCCUGU GU-3'

Human pre-miR-378
                                        (SEQ ID NO: 3)
5'- AGGGCUCCUG ACUCCAGGUC CUGUGUGUUA CCUAGAAAUA

GCACUGGACU UGGAGUCAGA AGGCCU-3'

Mouse mature miR-378
                                        (SEQ ID NO: 4)
5'-ACUGGACUUG GAGUCAGAAG G-3'

Mouse miR-378*
                                        (SEQ ID NO: 5)
5'- CUCCUGACUC CAGGUCCUGU GU-3'

Mouse pre-miR-378
                                        (SEQ ID NO: 6)
5'- AGGGCUCCUG ACUCCAGGUC CUGUGUGUUA CCUCGAAAUA

GCACUGGACU UGGAGUCAGA AGGCCU-3'
```

It is understood that all ribonucleic acid sequences disclosed herein can be converted to deoxyribonucleic acid sequences by substituting a thymidine base for a uridine base in the sequence. Likewise, all deoxyribonucleic acid sequences disclosed herein can be converted to ribonucleic acid sequences by substituting a uridine base for a thymidine base in the sequence. Deoxyribonucleic acid sequences, ribonucleic acid sequences, and sequences containing mixtures of deoxyribonucleotides and ribonucleotides of all sequences disclosed herein are included in the invention.

In one embodiment, the present invention provides a method of treating or preventing pathologic cardiac hypertrophy, cardiac remodeling, myocardial infarction, or heart failure in a subject in need thereof comprising administering to the subject an inhibitor of miR-378 and/or miR-378*. In some embodiments, the expression or activity of miR-378 and/or miR-378* is reduced in the heart cells of the subject following administration of the inhibitor. "Heart cells," as used herein, include cardiomyocytes, cardiac fibroblasts, and cardiac endothelial cells. In one particular embodiment, the expression or activity of miR-378 and/or miR-378* is reduced in cardiomyocytes of the subject following administration of the miR-378 and/or miR-378* inhibitor.

In another embodiment, the subject in need thereof may be at risk for developing pathologic cardiac hypertrophy, cardiac remodeling, heart failure, or myocardial infarction. Such a subject may exhibit one or more risk factors including, but not limited to, long standing uncontrolled hypertension, pulmonary arterial hypertension, uncorrected valvular disease, chronic angina, recent myocardial infarction, congenital predisposition to heart disease or pathological hypertrophy. The subject at risk may be diagnosed as having a genetic predisposition to cardiac hypertrophy or may have a familial history of cardiac hypertrophy. In some embodiments, the subject at risk may be diagnosed with obesity, type II diabetes, hyperlipidemia, or metabolic syndrome.

Preferably, administration of an inhibitor of miR-378 and/or miR-378* to the subject results in the improvement of one or more symptoms of cardiac hypertrophy, heart failure, or myocardial infarction in the subject, or in the delay in the transition from cardiac hypertrophy to heart failure. The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease-related morbidity or mortality.

The present invention also includes a method of treating or preventing a metabolic disorder in a subject in need thereof. In one embodiment, the method comprises administering to the subject an inhibitor of miR-378 and/or miR-378*, wherein the expression or activity of miR-378 and/or miR-378* is reduced in the cells of the subject following administration. The metabolic disorders that can be treated with the methods of the invention include, but are not limited to, metabolic syndrome, obesity, diabetes mellitus, diabetic nephropathy, insulin resistance, atherosclerosis, a lipid storage disorder (e.g., Niemann-Pick disease, Gaucher's disease, Farber disease, Fabry disease, Wolman disease, and cholesteryl ester storage disease), polycystic ovarian syndrome (PCOS), or aberrant glucose uptake and/or utilization. In one embodiment, the metabolic disorder is a glycogen storage disease (GSD). For instance, the methods of the invention provide treating or preventing any of the types of GSD (e.g., GSD type 0 and GSD type I to GSD type XIII) in a subject in need thereof by administering to the subject a miR-378 and/or miR-378* inhibitor. GSDs include, but are not limited to, von Gierke's disease, Pompe's disease, Cori's disease or Forbes' disease, Andersen disease, McArdle disease, Hers' disease, Tarui's disease, Fanconi-Bickel syndrome, and red cell aldolase deficiency. In another embodiment, the metabolic disorder is medium-chain acyl-coenzyme A dehydrogenase (MCAD) deficiency. Individuals having MCAD deficiency exhibit an impairment in fatty acid oxidation that can be fatal. In one embodiment of the invention, fatty acid metabolism is increased in subject's having MCAD deficiency following administration of a miR-378 and/or miR-378* inhibitor.

The present invention also includes a method of preventing or treating secondary diseases or conditions resulting from metabolic disorders, such as diabetes and obesity, by administering to a subject in need thereof of an inhibitor of miR-378 and/or miR-378*. For example, in one embodiment, the invention provides a method of preventing or treating sleep apnea comprising administering to a subject in need thereof an inhibitor of miR-378 and/or miR-378*. In another embodiment, the invention provides a method of preventing or treating cancer by administering to a subject in need thereof an inhibitor of miR-378 and/or miR-378*. In still another embodiment, the invention provides a method of preventing or treating osteoarthritis by administering to a subject in need thereof an inhibitor of miR-378 and/or miR-378*.

In another embodiment, the present invention encompasses a method of increasing glucose uptake and/or utilization in a subject in need thereof comprising administering to the subject an inhibitor of miR-378 and/or miR-378* activity or expression. In some embodiments, the subject is diagnosed with insulin resistance or diabetes mellitus. In one embodiment, the subject's blood glucose level is reduced following administration of the miR-378 and/or miR-378* inhibitor as compared to the blood glucose level of the subject prior to administration of the inhibitor. In another embodiment, the subject's blood glucose level is reduced to within normal levels as measured by the oral glucose tolerance test following administration of the miR-378 and/or miR-378* inhibitor. For instance, in certain embodiments, the subject's fasting blood glucose level is less than about 110 mg/dl. In other embodiments, the subject's blood glucose level 2 hours post glucose ingestion is less than about 140 mg/dl.

The present invention also provides a method of regulating fatty acid metabolism in a cell. In one embodiment, the method comprises contacting the cell with a modulator of miR-378 and/or miR-378* expression or activity. As used herein, a "modulator" is a molecule that regulates the expression or activity of miR-378 and/or miR-378*. Modulators can be agonists of miR-378 and/or miR-378* function (i.e. enhance the activity or expression of miR-378 or miR-378*) or they can be inhibitors of miR-378 and/or miR-378* function (i.e. reduce the activity or expression of miR-378 or miR-378*). Modulators can include proteins, peptides, polypeptides, polynucleotides, oligonucleotides, or small molecules. Modulators of miR-378 and/or miR-378* expression or activity include miR-378 and/or miR-378* inhibitors and agonists as described herein. In certain embodiments, the modulator is an inhibitor of miR-378 and/or miR-378* expression or activity, and fatty acid metabolism is increased in the cell following contact with the miR-378 and/or miR-378* inhibitor as compared to a cell not exposed to the inhibitor. In other embodiments, the modulator is an agonist of miR-378 and/or miR-378* expression or activity, and fatty acid metabolism is decreased in the cell following contact with the miR-378 and/or miR-378* agonist as compared to a cell not exposed to the agonist. The cell can be in vitro or in vivo. In some embodiments, the cell is, but is not limited to, a cardiomyocyte, a skeletal muscle cell, a preadipocyte, an adipocyte, a hepatocyte, or a pancreatic cell.

In one particular embodiment, the cell is a cardiomyocyte. Thus, the present invention also encompasses a method of regulating cardiac metabolism by contacting a cardiomyocyte with a modulator of miR-378 and/or miR-378* expression or activity. In one embodiment, contacting the cardiomyocyte with a miR-378 and/or miR-378* inhibitor prevents or reduces the metabolic shift from oxidative metabolism to glycolytic metabolism induced by a stressor. In another embodiment, contacting the cardiomyocyte with a miR-378 and/or miR-378* inhibitor reduces carbohydrate metabolism in the cardiomyocyte. In still another embodiment, contacting the cardiomyocyte with a miR-378 and/or miR-378* inhibitor increases fatty acid metabolism in the cardiomyocyte. The cardiomyocyte can be in vitro or in vivo.

In another aspect, the present invention encompasses a method of regulating mitochondrial dysfunction in a cell by contacting the cell with a modulator of miR-378 and/or miR-378* expression or activity. In one embodiment, contacting the cell with a miR-378 and/or miR-378* inhibitor increases mitochondrial biogenesis in the cell as compared to an untreated cell. In another embodiment, contacting the cell with a miR-378 and/or miR-378* inhibitor enhances mitochondrial fatty acid oxidation in the cell as compared to an untreated cell. In yet another embodiment, contacting the cell with a miR-378 and/or miR-378* agonist enhances lipogenesis in the cell as compared to an untreated cell. In still another embodiment, contacting the cell with a miR-378 and/or miR-378* agonist enhances glucose metabolism in the cell as compared to an untreated cell. The cell can be in vitro or in vivo. In certain embodiments, the cell is, but is not limited to, a cardiomyocyte, a skeletal muscle cell, a preadipocyte, an adipocyte, a hepatocyte, or a pancreatic cell.

The present invention also provides a method for preventing or treating disorders or diseases associated with a deficiency in glycolytic or fatty acid metabolism. For instance, in one embodiment, the present invention provides a method for preventing or treating hypoglycemia or hyperinsulinism in a subject in need thereof by administering to the subject a miR-378 and/or miR-378* agonist. Subjects at risk of developing hypoglycemia or hyperinsulinism include diabetic patients who overdose on insulin or certain diabetes medications (e.g., chlorpropamide, tolazamide, acetohexamide, glipizide, or tolbutamide), subject who have an insulin secreting tumor (insulinoma), patients diagnosed with liver disease or genetic conditions that cause hyperinsulinism. Other disorders or conditions that may be treated or prevented with agonists of miR-378 and/or miR-378* are those in which patients have difficulty maintaining a normal body weight or experience unintentional weight loss. For instance, in one embodiment, the present invention includes a method of treating or preventing hyperthyroidism (Graves' Disease) in a subject in need thereof by administering to the subject a miR-378 and/or miR-378* agonist.

In some embodiments, an inhibitor of miR-378 and/or miR-378* is an antisense oligonucleotide. The antisense oligonucleotides can include ribonucleotides or deoxyribonucleotides or a combination thereof. Preferably, the antisense oligonucleotides have at least one chemical modification (e.g., sugar or backbone modification). For instance, suitable antisense oligonucleotides can be comprised of one or more "conformationally constrained" or bicyclic sugar nucleoside modifications (BSN) that confer enhanced thermal stability to complexes formed between the oligonucleotide containing BSN and their complementary microRNA target strand. For example, in one embodiment, the antisense oligonucleotides contain at least one "locked nucleic acid." Locked nucleic acids (LNAs) contain the 2'-O, 4'-C-methylene ribonucleoside (structure A) wherein the ribose sugar moiety is in a "locked" conformation. In another embodiment, the antisense oligonucleotides contain at least one 2', 4'-C-bridged 2' deoxyribonucleoside (CDNA, structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miR-378 can contain combinations of BSN (LNA, CDNA and the like) or other modified nucleotides, and ribonucleotides or deoxyribonucleotides.

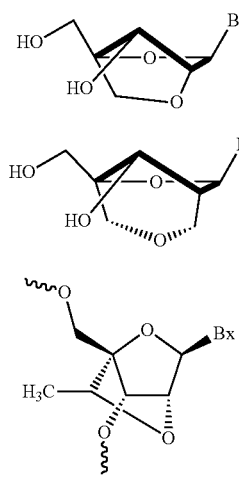

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. For instance, other chemical modifications that the antisense oligonucleotides can contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In one embodiment, antisense oligonucleotides targeting miR-378 or miR-378* contain 2'O-methyl sugar modifications on each base and are linked by phosphorothioate linkages. Antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O-alkyl modifications and the like. In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

Preferable antisense oligonucleotides useful for inhibiting the activity of miRNAs are about 5 to about 25 nucleotides in length, about 10 to about 30 nucleotides in length, or about 20 to about 25 nucleotides in length. In certain embodiments, antisense oligonucleotides targeting miR-378 and/or miR-378* are about 7 to about 18 nucleotides in length, and in other embodiments about 12 to about 16 nucleotides in length. Any 7-mer or longer complementary to miR-378 or miR-378* may be used, i.e., any antimiR complementary to the 5' end of the miRNA and progressing across the full complementary sequence of the miRNA. For instance, in one embodiment, the antisense oligonucleotide has a sequence of 5'-CCUUCUGACUCCAAGUCCAGU-3' (SEQ ID NO: 7). In another embodiment, the antisense oligonucleotide has a sequence of 5'-AGUCCAGU-3' (SEQ ID NO: 8). In another embodiment, the antisense oligonucleotide has a sequence of 5'-CAAGUCCAGU-3' (SEQ ID NO: 9). In another embodiment, the antisense oligonucleotide has a sequence of 5'-UCCAAGUCCAGU-3' (SEQ ID NO: 10). In yet another embodiment, the antisense oligonucleotide has a sequence of 5'-ACUCCAAGUCCAGU-3' (SEQ ID NO: 11). In still another embodiment, the antisense oligonucleotide has a sequence of 5'-UGACUCCAAGUCCAGU-3' (SEQ ID NO: 12) or 5-CUGACUCCAAGUCCAG-3' (SEQ ID NO: 13). In certain embodiments, the antisense oligonucleotide has a sequence of 5'-TGACTCCAAGTCCAG-3' (SEQ ID NO: 21).

Exemplary antisense oligonucleotides for inhibiting miR-378* expression or activity include, but are not limited to, 5'-ACACAGGACCUGGAGUCAGGAG-3' (SEQ ID NO: 14); 5'-GUCAGGAG-3' (SEQ ID NO: 15); 5'-GAGUCAGGAG-3' (SEQ ID NO: 16); 5'-UGGAGUCAGGAG-3' (SEQ ID NO: 17); 5'-CCUGGAGUCAGGAG-3' (SEQ ID NO: 18); 5'-GACCUGGAGUCAGGAG-3' (SEQ ID NO: 19); 5'-GGACCUGGAGUCAGGA-3' (SEQ ID NO: 20), and 5'-GACCTGGAGTCAGGA-3'(SEQ ID NO: 22).

Antisense oligonucleotides can comprise a sequence that is at least partially complementary to a mature or minor (i.e. star) miR-378 sequence, e.g. at least about 75%, 80%, 85%, 90%, 95%, 96%, 97%, 98%, or 99% complementary to a mature or minor (i.e. star) miR-378 sequence. In some embodiments, the antisense oligonucleotide can be substantially complementary to a mature or minor miR-378 sequence, that is at least about 90%, 95%, 96%, 97%, 98%, or 99% complementary to a target polynucleotide sequence. In one embodiment, the antisense oligonucleotide comprises a sequence that is 100% complementary to a mature or minor miR-378 sequence. In certain embodiments, the antisense oligonucleotide is at least partially complementary to SEQ ID NO: 1. In other embodiments, the antisense oligonucleotide is at least partially complementary to SEQ ID NO: 2.

In some embodiments, the antisense oligonucleotides are antagomirs. "Antagomirs" are single-stranded, chemically-modified ribonucleotides that are at least partially complementary to a miR-378 or miR-378* sequence. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting miR-378 or miR-378* can be about 15 to about 50 nucleotides in length, more preferably about 18 to about 30 nucleotides in length, and most preferably about 20 to about 25 nucleotides in length. The antagomirs can be at least about 75%, 80%, 85%, 90%, 95%, 96%, 97%, 98%, or 99% complementary to a mature or minor miR-378 sequence. In some embodiments, the antagomir may be substantially complementary to a mature or minor miR-378 sequence, that is at least about 95%, 96%, 97%, 98%, or 99% complementary to a target polynucleotide sequence. In other embodiments, the antagomirs are 100% complementary to a mature or minor miR-378 sequence.

The inhibitory nucleotide molecules described herein preferably target the mature sequence of miR-378 (SEQ ID NO: 1). In one embodiment, the inhibitory nucleotide molecules described herein target the minor (i.e. miR-378*) sequence of miR-378 (SEQ ID NO: 2). In some embodiments, inhibitors of miR-378 and/or miR-378* are antagomirs comprising a sequence that is perfectly complementary to the mature or minor miR-378 sequence. In one embodiment, an inhibitor of miR-378 is an antagomir having a sequence that is partially or perfectly complementary to 5'-ACUGGACUUGGAGUCA-GAAGG-3' (SEQ ID NO: 1). In another embodiment, an inhibitor of miR-378* is an antagomir having a sequence that is partially or perfectly complementary to 5'-CUC-CUGACUCCAGGUCCUGUGU-3' (SEQ ID NO: 2). In some embodiments, inhibitors of miR-378 and/or miR-378* are chemically-modified antisense oligonucleotides. In one embodiment, an inhibitor of miR-378 is a chemically-modified antisense oligonucleotide comprising a sequence substantially complementary to 5'-ACUGGACUUGGAGUCA-GAAGG-3' (SEQ ID NO: 1). In another embodiment, an inhibitor of miR-378* is a chemically-modified antisense oligonucleotide comprising a sequence substantially complementary to 5'-CUCCUGACUCCAGGUCCUGUGU-3' (SEQ ID NO: 2). As used herein "substantially complementary" refers to a sequence that is at least about 95%, 96%, 97%, 98%, 99%, or 100% complementary to a target polynucleotide sequence (e.g. mature, minor, or precursor miRNA sequence).

Antisense oligonucleotides or antagomirs may comprise a sequence that is substantially complementary to a precursor miRNA sequence (pre-miRNA) or primary miRNA sequence (pri-miRNA) for miR-378. In some embodiments, the antisense oligonucleotide comprises a sequence that is substantially complementary to a sequence located outside the stem-loop region of the pre-miR-378 sequence. In one embodiment, an inhibitor of miR-378 function is an antisense oligonucleotide having a sequence that is substantially complementary to a pre-miR-378 sequence (SEQ ID NO: 3).

An agonist of miR-378 and/or miR-378* expression or activity can be a polynucleotide comprising a miR-378 and/or miR-378* sequence. For instance, in one embodiment the miR-378 agonist is a polynucleotide comprising a mature miR-378 sequence (SEQ ID NO: 1). In another embodiment, the miR-378* agonist is a polynucleotide comprising a minor (i.e. star) miR-378 sequence (SEQ ID NO: 2). In still another embodiment, the miR-378 agonist can be a polynucleotide comprising the pri-miRNA sequence for miR-378. In yet another embodiment, the miR-378 and/or miR-378* agonist can be a polynucleotide comprising the pre-miRNA sequence for miR-378 (e.g., SEQ ID NO: 3). The polynucleotide comprising a miR-378 and/or miR-378* sequence can be from about 18 to about 2000 nucleotides in length, about 70 to about 200 nucleotides in length, about 20 to about 50 nucleotides in length, or about 18 to about 25 nucleotides in length. The polynucleotide comprising the mature miR-378, minor miR-378 (i.e. miR-378*), pre-miR-378, or pri-miR-378 sequence can be single stranded or double-stranded. The polynucleotides can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-378 sequence (e.g., mature miR-378, miR-378*, pre-miR-378, or pri-miR-378) is conjugated to a steroid, such as cholesterol, a vitamin, a fatty acid, a carbohydrate or glycoside, a peptide, or another small molecule ligand.

Any of the inhibitors or agonists of miR-378 and/or miR-378* described herein can be delivered to the target cell (e.g. heart, adipose, or skeletal muscle cell) by delivering to the cell an expression vector encoding the miR-378 inhibitors or agonists. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an inhibitor of miR-378 and/or miR-378* comprises a promoter operably linked to a polynucleotide encoding an antisense oligonucleotide, wherein the sequence of the expressed antisense oligonucleotide is partially or perfectly complementary to a mature or minor sequence of miR-378 (e.g., SEQ ID NO: 1 or SEQ ID NO: 2). In another embodiment, an expression vector for expressing a polynucleotide comprising a miR-378 sequence comprises a promoter operably linked to a polynucleotide comprising a mature miR-378 sequence (e.g., SEQ ID NO: 1), a minor miR-378 sequence (e.g., SEQ ID NO: 2), a pre-miR-378 sequence (e.g., SEQ ID NO: 3), or a pri-miR-378 sequence. The phrase "operably linked" or "under transcriptional control" as used herein means that the promoter is in the correct location and orientation in relation to a polynucleotide to control the initiation of transcription by RNA polymerase and expression of the polynucleotide.

As used herein, a "promoter" refers to a DNA sequence recognized by the synthetic machinery of the cell, or introduced synthetic machinery, required to initiate the specific transcription of a gene. Suitable promoters include, but are not limited to RNA pol I, pol II, pol HI, and viral promoters (e.g. human cytomegalovirus (CMV) immediate early gene promoter, the SV40 early promoter, and the Rous sarcoma virus long terminal repeat). In one embodiment, the promoter is a tissue-specific promoter. Of particular interest are muscle specific promoters, and more particularly, cardiac specific promoters. These include the myosin light chain-2 promoter (Franz et al. (1994) *Cardioscience*, Vol. 5(4):235-43; Kelly et al. (1995) *J. Cell Biol.*, Vol. 129(2):383-396), the alpha actin promoter (Moss et al. (1996) *Biol. Chem.*, Vol. 271(49): 31688-31694), the troponin 1 promoter (Bhaysar et al. (1996)

*Genomics*, Vol. 35(1):11-23); the Na+/Ca2+ exchanger promoter (Barnes et al. (1997) *J. Biol. Chem.*, Vol. 272(17): 11510-11517), the dystrophin promoter (Kimura et al. (1997) *Dev. Growth Differ.*, Vol. 39(3):257-265), the alpha7 integrin promoter (Ziober and Kramer (1996) *J. Bio. Chem.*, Vol. 271(37):22915-22), the brain natriuretic peptide promoter (LaPointe et al. (1996) *Hypertension*, Vol. 27(3 Pt 2):715-22) and the alpha B-crystallin/small heat shock protein promoter (Gopal-Srivastava (1995) *J. Mol. Cell. Biol.*, Vol. 15(12): 7081-7090), alpha myosin heavy chain promoter (Yamauchi-Takihara et al. (1989) *Proc. Natl. Acad. Sci. USA*, Vol. 86(10): 3504-3508) and the ANF promoter (LaPointe et al. (1988) *J. Biol. Chem.*, Vol. 263(19):9075-9078). In one embodiment, the tissue-specific promoter is an adipocyte-specific promoter, such as an adipocyte protein 2 (ap2)/fatty acid binding protein 4 (FABP4) promoter or a PPARγ promoter.

In certain embodiments, the promoter operably linked to a polynucleotide encoding a miR-378 and/or miR-378* inhibitor or a polynucleotide encoding a miR-378 sequence can be an inducible promoter. Inducible promoters are known in the art and include, but are not limited to, tetracycline promoter, metallothionein IIA promoter, heat shock promoter, steroid/thyroid hormone/retinoic acid response elements, the adenovirus late promoter, and the inducible mouse mammary tumor virus LTR.

Methods of delivering expression constructs and nucleic acids to cells are known in the art and can include, for example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes methods for scavenging or clearing miR-378 and/or miR-378* inhibitors following treatment. The method may comprise overexpressing binding sites for the miR-378 and/or miR-378* inhibitors in cardiac or skeletal muscle tissue. The binding site regions preferably contain a sequence of the seed region for miR-378 and/or miR-378*. The seed region is the 5' portion of a miRNA spanning bases 2-8, which is important for target recognition. In some embodiments, the binding site may contain a sequence from the 3'UTR of one or more targets of miR-378 and/or miR-378*, such as SuFu, Fus-1, glutamine:fructose-6-phosphate amidotransferase-2 (GFPT2), and MED 13.

The present invention also includes pharmaceutical compositions comprising an inhibitor or agonist of miR-378 and/or miR-378*. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of a miR-378 and/or miR-378* inhibitor and a pharmaceutically acceptable carrier. For instance, the pharmaceutical composition comprises and effective dose of a modified antisense oligonucleotide targeting miR-378 and/or miR-378* as described herein. In some embodiments, the pharmaceutical composition comprises a modified antisense oligonucleotide having a sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22. In another embodiment, the pharmaceutical composition comprises an effective dose of a miR-378 and/or miR-378* agonist as described herein and a pharmaceutically acceptable carrier. An "effective dose" is an amount sufficient to effect a beneficial or desired clinical result. An effective dose of an miRNA inhibitor or miRNA agonist of the invention may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of disorder (e.g. myocardial infarction, heart failure, cardiac hypertrophy, metabolic disorder), and nature of inhibitor or agonist (e.g. antagomir, expression construct, antisense oligonucleotide, polynucleotide duplex, etc). Therefore, dosages can be readily ascertained by those of ordinary skill in the art from this disclosure and the knowledge in the art.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of miR-378 and/or miR-378* function, polynucleotides encoding miR-378 and/or miR-378* agonists, or constructs expressing particular miRNA inhibitors or agonists. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising miRNA inhibitors, miRNA agonists or expression constructs comprising miRNA inhibitors or agonists may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In certain embodiments of the invention, the pharmaceutical compositions of the invention are packaged with or stored within a device for administration. Devices for injectable formulations include, but are not limited to, injection ports, autoinjectors, injection pumps, and injection pens. Devices for aerosolized or powder formulations include, but are not limited to, inhalers, insufflators, aspirators, and the like. Thus, the present invention includes administration devices comprising a pharmaceutical composition of the invention for treating or preventing one or more of the disorders described herein.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1 miR-378/miR-378* is Highly Expressed in Mitochondrial-Rich Tissues

Expression profiling of miRNAs in the failing heart has been described previously using mouse models of heart disease (van Rooij et al. (2006) Proc. Natl. Acad. Sci. USA, Vol. 103:18255-18260). MicroRNA microarray analysis carried out in tissue obtained from hearts with hypertrophy induced by pressure overload, calcineurin overexpression or isoproterenol administration revealed that miR-378 (GeneID:

723889) is one of the most robustly regulated miRNAs under these conditions. MiR-378 is also down-regulated in myocardial infarction (van Rooij et al. (2008) Proc. Natl. Acad. Sci. USA, Vol. 105:13027-13032), providing further evidence that miR-378 is an important determinant of the cardiac stress-response program. MiR-378 is located on murine chromosome 18, within the first intron of the Peroxisome proliferator-activated receptor gamma coactivator 1-beta (PPARGC1β, GeneID: 170826) gene (FIG. 1A).

Figure 1E:
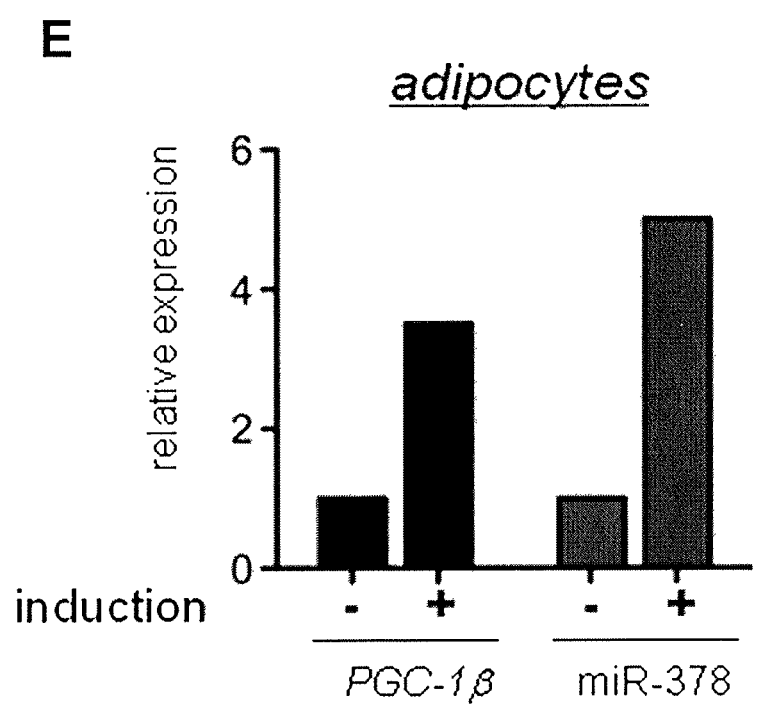

To examine the expression profile of miR-378 and miR-378*, quantitative real time PCR analysis of various tissues isolated from mice was performed. MiR-378 and miR-378* were found to be highly expressed in heart, skeletal muscle, and brown adipose tissue (FIG. 1B). In heart tissue, miR-378 was more highly expressed in cardiomyocytes than in cardiac fibroblasts (FIG. 1C). The expression pattern of miR-378/miR-378* and their host gene, PPARGC1β (PGC-1β), were overlapping (FIG. 1B), suggesting that miR-378/miR-378* and PPARGC1β are co-transcribed. Consistent with this hypothesis, a reduction in the expression level of miR-378 was observed in cell culture upon treatment with stearic acid, a known repressor of PPARGC1β expression (FIG. 1D). The expression of both miR-378 and its host gene, PPARGC1β (PGC-1β), is increased during adipogenesis (FIG. 1E). It has been shown that acute elevation of plasma levels of stearic acid, as well as other short chain fatty acids down-regulates PPARGC1α, PPARGC1β and PPARα expression (Staiger et al. (2005) Diabetologia, Vol. 48:2115-2118). The observation that the transcription of both miR-378 and the host gene PPARGC1β follow parallel regulatory patterns strongly suggests that the two genes are co-regulated. PPARGC1β is known to play a role in the regulation of fatty acid oxidation, glucose utilization, and mitochondrial biogenesis (Handschin and Spiegelman (2006) Endocr. Rev., Vol. 27:728-735; Lelliott et al. (2006) PLoS Biol., Vol. 4:2042-2056; Luptak et al. (2005) Circulation, Vol. 112:2339-2346; Sonoda et al. (2007) Proc. Natl. Acad. Sci. USA, Vol. 104:5223-5228; and Vianna et al. (2006) Cell Metab., Vol. 4:453-464). It is likely that miR-378/miR-378* play a role in these same processes as intronic miRNAs often participate in the same network of gene programs as their host gene.

Example 2

MiR-378 Regulates the Stress-Induced Cardiac Hypertrophic Response

To further elucidate the role of miR-378 in cardiac disease, miR-378 expression was assessed in heart tissue after induction of cardiac hypertrophy by thoracic aortic banding (TAB) in wild-type mice. Specifically, the aorta was sutured to the diameter of a 27-gauge needle, inducing pressure overload on the heart, thus mimicking hypertension. Control animals were subject to a sham surgery in which the aorta was not altered. MicroRNA microarray analysis and real-time PCR of cardiac tissue isolated 21 days following the TAB procedure revealed that miR-378 is down-regulated in response to pressure overload (FIG. 2A).

To examine the effect of overexpression of miR-378 during heart disease, transgenic mice were generated that overexpress miR-378/miR-378* under the control of the cardiomyocyte-specific α-myosin heavy chain (α-MHC) promoter. Following TAB, these transgenic animals displayed an exacerbated cardiac hypertrophic response compared to wild-type mice (FIG. 2B). These findings show that the forced expression of miR-378 during heart disease is deleterious to the heart and the decrease of miR-378 in wild-type mice following TAB is suggestive of a protective response of the heart against the applied stress.

MiR-378 is likely to play a role in the process of cardiac metabolism, specifically the hypertrophic metabolic shift (Luptak et al. (2005) Circulation, Vol. 112:2339-2346). We suggest that miR-378 augments the cardiac metabolic shift and thus participates in the cardiac hypertrophic response under stress. Inhibition of miR-378 expression or activity may provide a therapeutic benefit in patients with cardiovascular diseases.

Example 3

Figure 3:
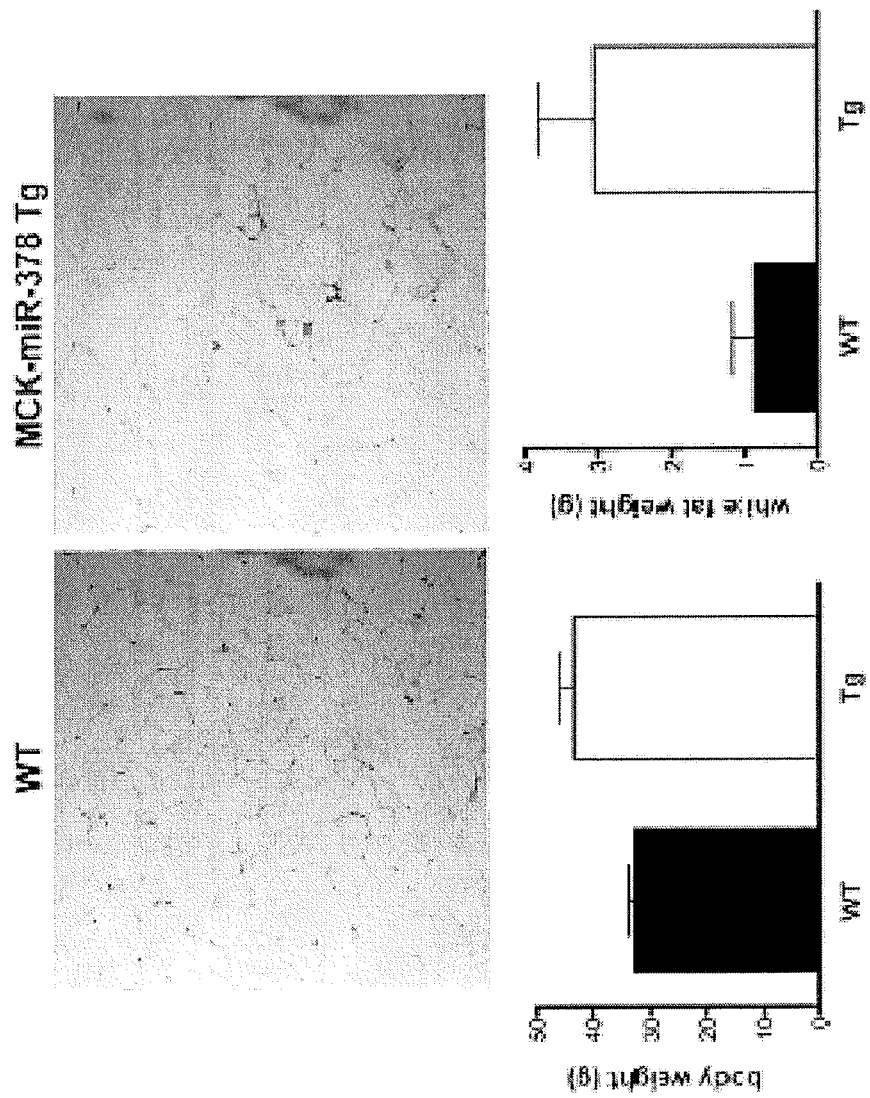
FIG. 3. Overexpression of miR-378 in the skeletal muscle results in increased body weight and epididymal fat mass. Top panels show histological analysis of white fat tissue from wild-type (WT) mice and mice overexpressing miR-378 under the control of the MCK promoter (MCK-miR-378 Tg). Mutant animals display hypertrophic adipocytes. Lower panels show increased body weight and increased white fat mass in the MCK-miR-378 transgenic mice compared to wild-type mice.

Overexpression of miR-378 in Skeletal Muscle Results in Increased Body Weight and Epididymal Fat Mass To examine the effect of the overexpression of miR-378 in the skeletal muscle, transgenic mice were generated that overexpress miR-378/miR-378* under the control of the muscle creatine kinase (MCK) promoter. Preliminary investigation of the MCK-miR-378 transgenic animals revealed that miR-378 modulates glucose and fatty acid utilization. In particular, older age (10 months of age) transgenic animals weighed significantly more than wild-type littermates (FIG. 3). The difference in body weight resulted from increased weight of epididymal white fat pads in mutant animals as compared to wild-type animals (FIG. 3). Histological analysis of the white fat tissue showed adipocyte hypertrophy in miR-378-overexpressing mice (FIG. 3). The increased accumulation of triglycerides in the adipocytes of MCK-miR-378 transgenic animals is likely the consequence of increased insulin resistance and global defects in glucose utilization.

Figure 4:
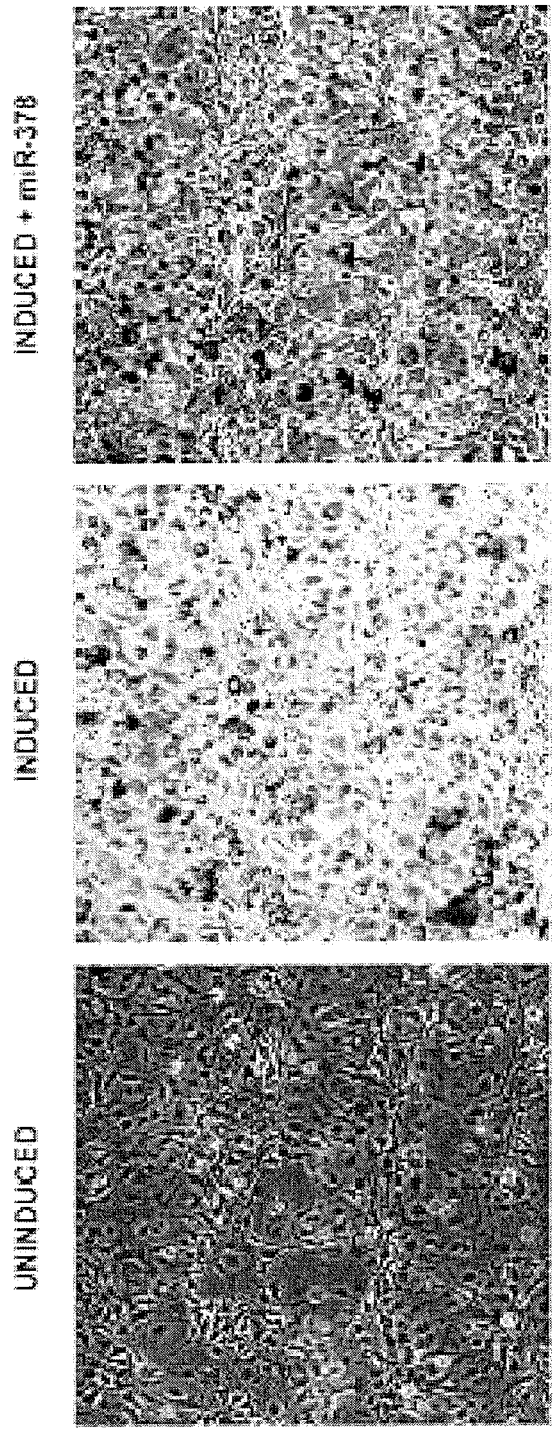
FIG. 4. Overexpression of miR-378 in 3T3-L1 cells enhances adipogenesis and lipogenesis. 313-L1 cells were induced to differentiate into mature adipocytes for 4 days. Transfection of miR-378 increased the accumulation of lipids within the cells, as demonstrated by Oil red O staining.

In another series of experiments, miR-378 was overexpressed in 3T3-L1 cells, which were subsequently induced to differentiate into adipocytes. As demonstrated by Oil red O staining, increased lipid accumulation was observed in cells overexpressing miR-378 providing further evidence of the involvement of miR-378 in the regulation of metabolic processes (FIG. 4).

Microarray analysis of various tissues isolated from obese mice (ob/ob) and diabetes mice (db/db) revealed that miR-378 is strongly down-regulated (data not shown). Ob/ob mice have a mutation in the gene encoding leptin, which causes them to be unable to produce the leptin hormone and properly regulate appetite. Db/db mice have a mutation in the gene encoding the leptin receptor that causes an abnormal splicing of the transcript leading to truncation of the cellular domain of the receptor. The mutant leptin receptor lacks signal transduction function. We suggest that the regulation of miR-378 in these animal models of obesity and diabetes represents a protective mechanism against the metabolic disorders induced by the disruption of leptin signaling. Thus, miR-378 may represent an effective therapeutic target for various metabolic disorders.

Example 4

Figure 5:
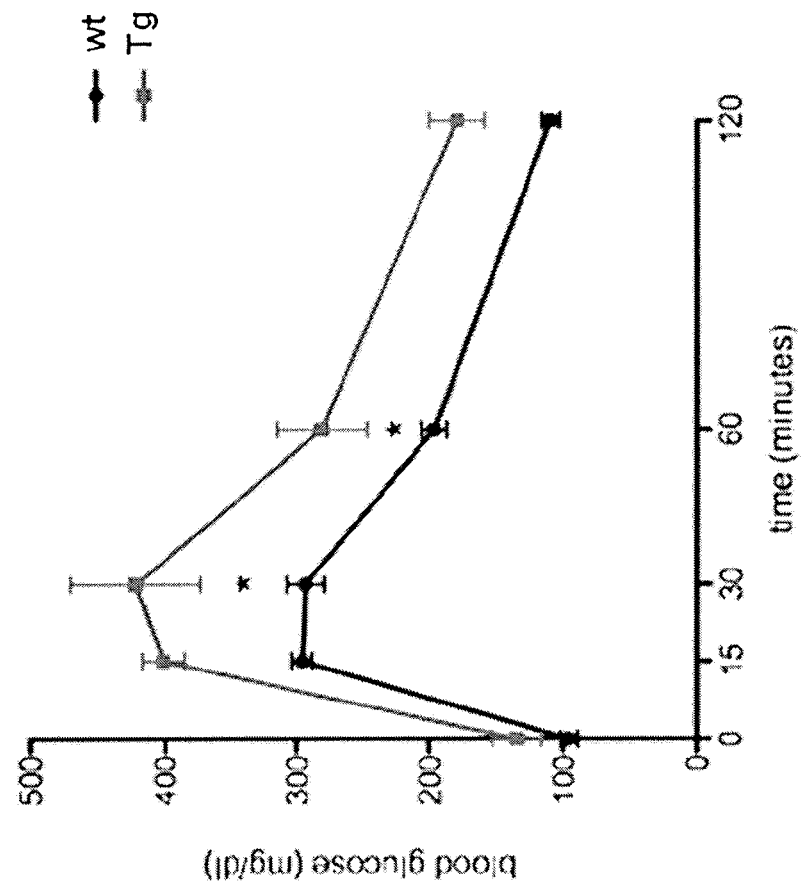
FIG. 5. MCK-miR-378 transgenic mice exhibit reduced glucose tolerance. Mice expressing miR-378 under the control of the muscle creatine kinase (MCK) promoter (Tg) or wild-type littermates (wt) were injected i.p. with 1.5 g/kg glucose after being fasted for 16 hours. Blood glucose levels were assessed at the indicated time points.

Transgenic Mice Overexpressing miR-378 in Skeletal Muscle Exhibit Reduced Glucose Tolerance To further examine the role of miR-378 in regulation of glucose utilization, transgenic mice overexpressing miR-378 in skeletal muscle (MCK-miR-378 Tg; see Example 3) were subject to a glucose tolerance test (GTT) to detect any potential deficits in clearance of glucose from the blood. Mice fasted for 16 hours and were subsequently injected intraperitoneally (i.p.) with 1.5 g/kg of glucose. Blood samples were obtained before glucose injection and 15, 30, 60, and 120 minutes following glucose injection. As shown in FIG. 5, blood glucose levels were elevated in miR-378 transgenic mice and clearance of glucose from the blood was delayed as compared to wild-type mice. These results show that overexpression of miR-378 in skeletal muscle leads to reduced glucose tolerance possibly due to increased insulin resistance in these animals.

Figure 6:
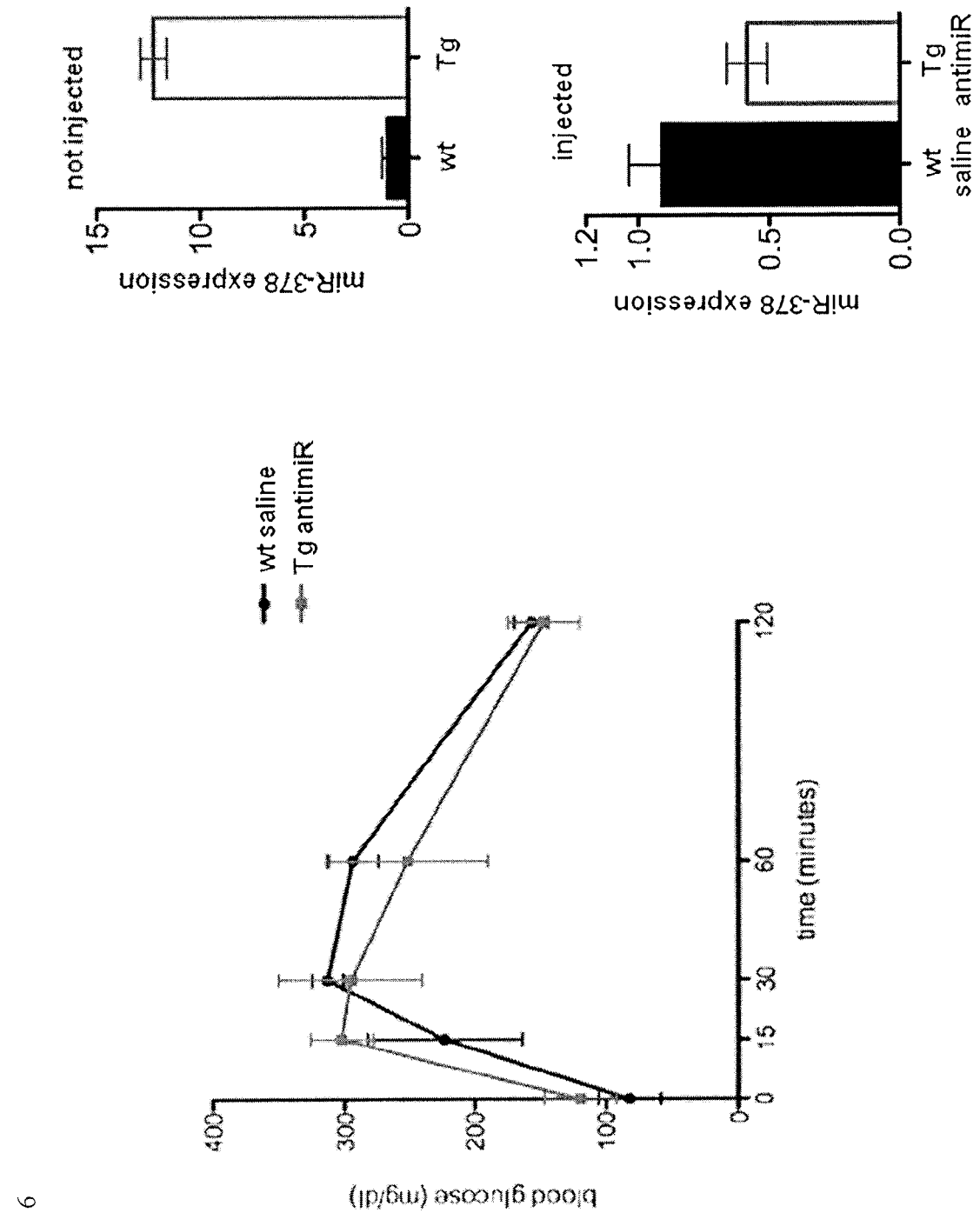
FIG. 6. AntimiR-378 injection in MCK-miR-378 transgenic mice improves glucose clearance. Mice expressing miR-378 under the control of the muscle creatine kinase (MCK) promoter (Tg) were injected i.v. on three consecutive days with 10 mg/kg of an antisense oligonucleotide having a sequence complementary to the miR-378 mature sequence (antmiR). Wild-type (wt) mice were injected with saline. Both Tg and wt mice were subsequently injected i.p. with 1.5 g/kg glucose after being fasted for 16 hours. Blood glucose levels were assessed at the indicated time points (left panel). Real-time PCR analysis for miR-378 expression in Tg and wt mice injected with antimiR-378 or saline (right panels).

To determine whether the effect on glucose tolerance was due specifically to miR-378 overexpression, MCK-miR-378 transgenic animals were injected via the tail vein with 10 mg/kg of antimiR-378 for three consecutive days. AntimiR-378 had a sequence that was complementary to nucleotides 2-16 of the mature miR-378 sequence (5'-TGACTC-CAAGTCCAG-3' (SEQ ID NO: 21)) and contained a combination of locked nucleic acids and deoxyribonucleotides (8 LNAs and 7 DNAs). AntimiR-378 contained a full phosphorothioate backbone. Following the last injection of antimiR-378, mice were fasted for 16 hours. Glucose (1.5 g/kg) was injected i.p. and blood samples were obtained before and at various time points following glucose injection. AntimiR-378 effectively reduced expression of miR-378 in transgenic mice to levels below those observed in saline-injected wild-type mice (FIG. 6). AntimiR-378 treatment of transgenic animals improved glucose clearance such that these animals exhibited a similar response as wild-type animals to the glucose tolerance test. These results suggest that the aberrant glucose utilization in miR-378 transgenic mice was due to overexpression of miR-378 and that normal metabolic processes can be restored by reducing the expression of miR-378.

Figure 7:
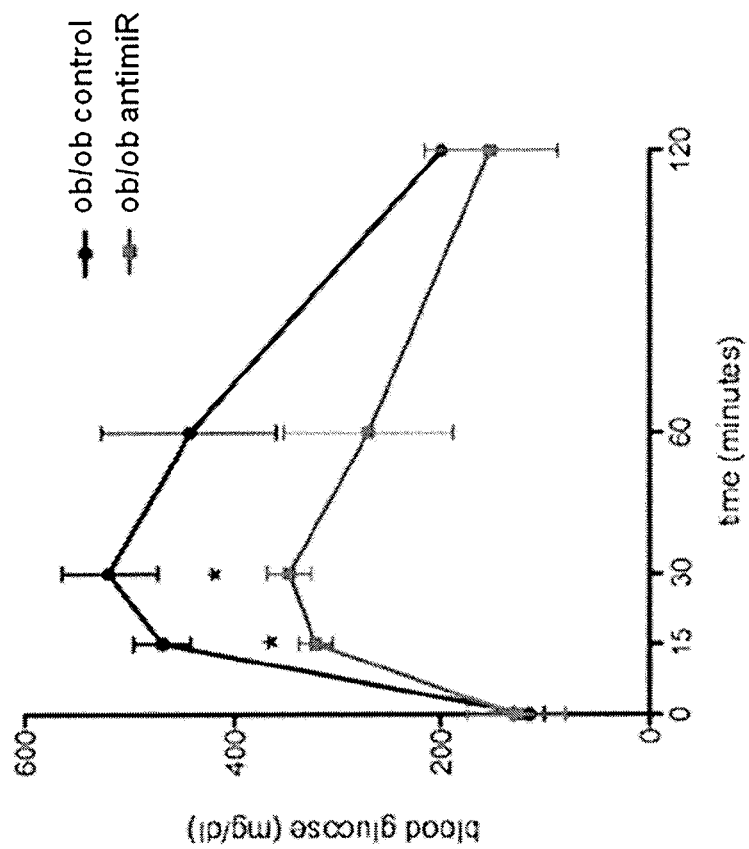
FIG. 7. AntimiR-378 injection in ob/ob mice improves glucose clearance. Obese mice (ob/ob) were injected i.v. on three consecutive days with 10 mg/kg of an antisense oligonucleotide having a sequence complementary to the miR-378 mature sequence (antmiR). Untreated and antimiR-treated ob/ob mice were injected i.p. with 1.5 g/kg glucose after being fasted for 16 hours. Blood glucose levels were assessed at the indicated time points.

To test whether antimiR-378 could restore normal glucose utilization in a mouse model of type 2 diabetes, obese (ob/ob) mice were injected intravenously with 10 mg/kg of antimiR-378 for three consecutive days. Following the last antimiR-378 injection, mice were fasted for 16 hours and injected i.p. with 1.5 g/kg glucose. Blood samples were obtained at various intervals after injection to assess blood glucose level. As shown in FIG. 7, ob/ob mice treated with antimiR-378 exhibited improved glucose clearance as compared to untreated animals. These findings demonstrate that inhibition of miR-378 expression is able to improve glucose utilization in animals with chronic disruption of leptin signaling. Therefore, miR-378 inhibitors provide a novel therapeutic approach for treating metabolic disorders, such as diabetes and obesity.

Example 5

Generation of miR-378 Knockout Mice

Figure 8A:
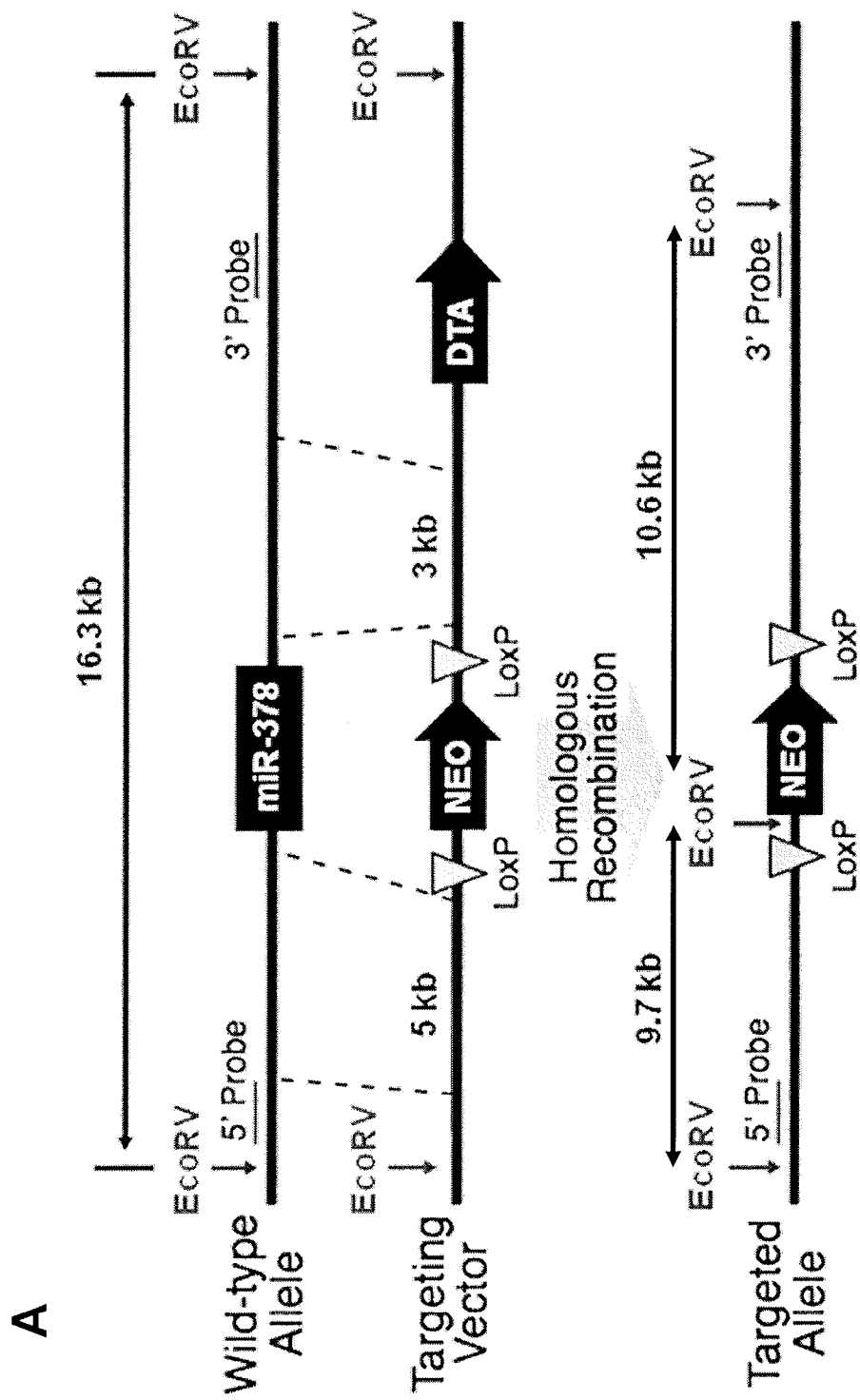
FIG. 8. A. MiR-378 targeting strategy. A targeting construct was introduced into the genomic miR-378 locus, yielding homologous recombination. B. Southern blot analysis of wild-type (WT) and targeted ES cells (MUT). C. Northern blot analysis performed using total RNA from wild-type (+/+), heterozygote (+/−), and knockout (−/−) mice shows that miR-378 expression (arrow) is abolished in the mutant mouse line generated. H: heart, BAT: brown adipose tissue, Sk.M: skeletal muscle. D. Real time PCR (left panel) and Western blot analysis (right panel) of heart tissue isolated from WT and miR-378 knockout (KO) mice shows that expression of the miR-378 host gene, PPARGC1β (PGC-1β), is not significantly altered in miR-378 knockout animals.
Figure 8D:
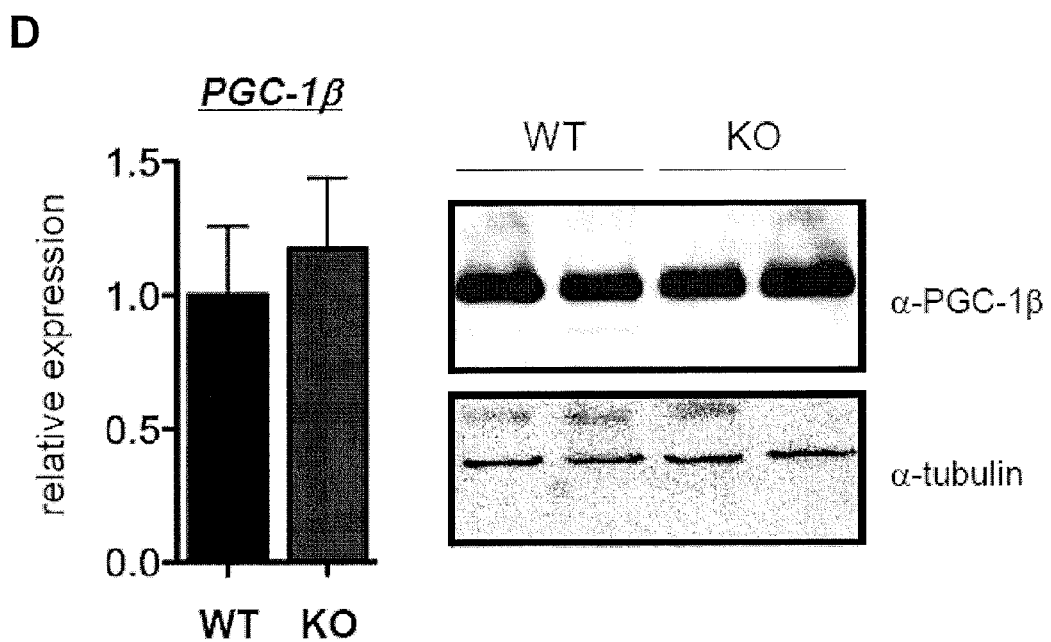

To determine the function of miR-378/miR-378* in vivo, a mouse line with a genetic deletion of miR-378/miR-378* was generated. Using a targeting vector and homologous recombination (FIG. 8A), miR-378/miR-378* was targeted and germline transmission of the genetic deletion was confirmed using Southern blot analysis (FIG. 8B). Northern blot analysis confirmed loss of miR-378/miR-378* expression in all tissues examined in the miR-378 global mutant (FIG. 8C). Real time PCR analysis using a Taqman probe for PPARGC1b and Western Blot analysis for PPARGC1β (PGC-1β) showed that PPARGC1β (PGC-1β) expression is not altered in the miR-378 knockout animal (FIG. 8D).

To determine the effect of miR-378 loss of function on cardiac remodeling, thoracic aortic banding (TAB) was performed on wild-type and miR-378 global knockout mice. Echocardiography was performed to determine fractional shortening, a measure of cardiac contractility and function, ejection fraction, systolic diameter, and diastolic-systolic diameter (DD-SD) on day 21 post TAB. Hearts were harvested one day after echocardiography. Histology was performed to determine cellular morphology. Expression of cardiac remodeling/stress genes, such as ANF, BNP, Myh7, Myh6, and collagen, was measured by real-time quantitative PCR.

Figure 9:
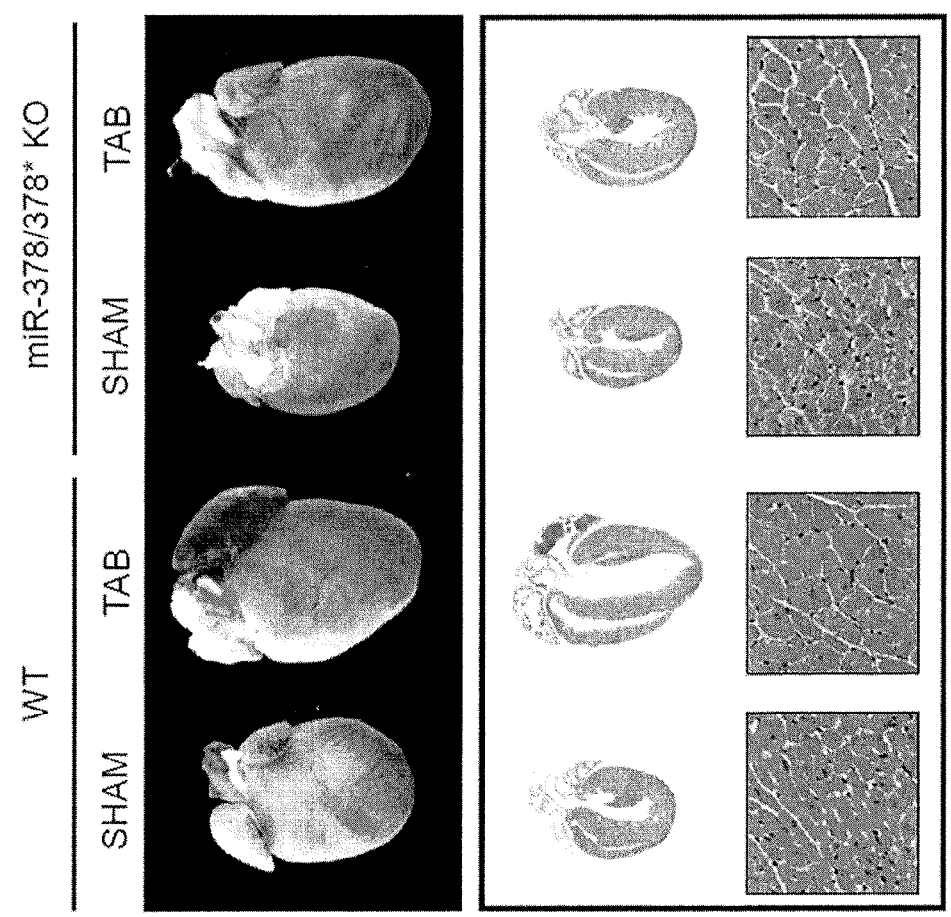
FIG. 9. MiR-378 knockout animals exhibit reduced cardiac hypertrophy in response to thoracic aortic banding (TAB).

The results of this series of experiments show that miR-378 knockout animals were protected from TAB-induced cardiac remodeling. Hearts from knockout animals exhibited reduced myocyte hypertrophy and cardiac fibrosis measured by histologic analysis when compared to wild-type mice (FIG. 9). Similarly, the miR-378 knockouts were protected from a decrease in cardiac contractility and function as measured by echocardiography (FIG. 10A-D). The miR-378 knockout animals also exhibited attenuation of remodeling/stress gene up-regulation (FIG. 11A-C). These results demonstrate that miR-378 is a positive regulator of cardiac hypertrophy/remodeling and inhibiting miR-378 expression and activity represents a novel therapeutic approach for reducing pathological remodeling in response to cardiac stressors.

The miR-378 knockout mice are also crossed to animals overexpressing the pro-hypertrophic phosphatase calcineurin, which induces a form of hypertrophic cardiomyopathy. In addition, the cardiac hypertrophic agonist isoproterenol or saline (control) is administered to miR-378 knockout mice to determine the effect of loss of miR-378 in cardiac remodeling. MiR-378 knockout animals are expected to be protected from isoproterenol and calcineurin-induced cardiac remodeling as well.

Example 6

Figure 12:
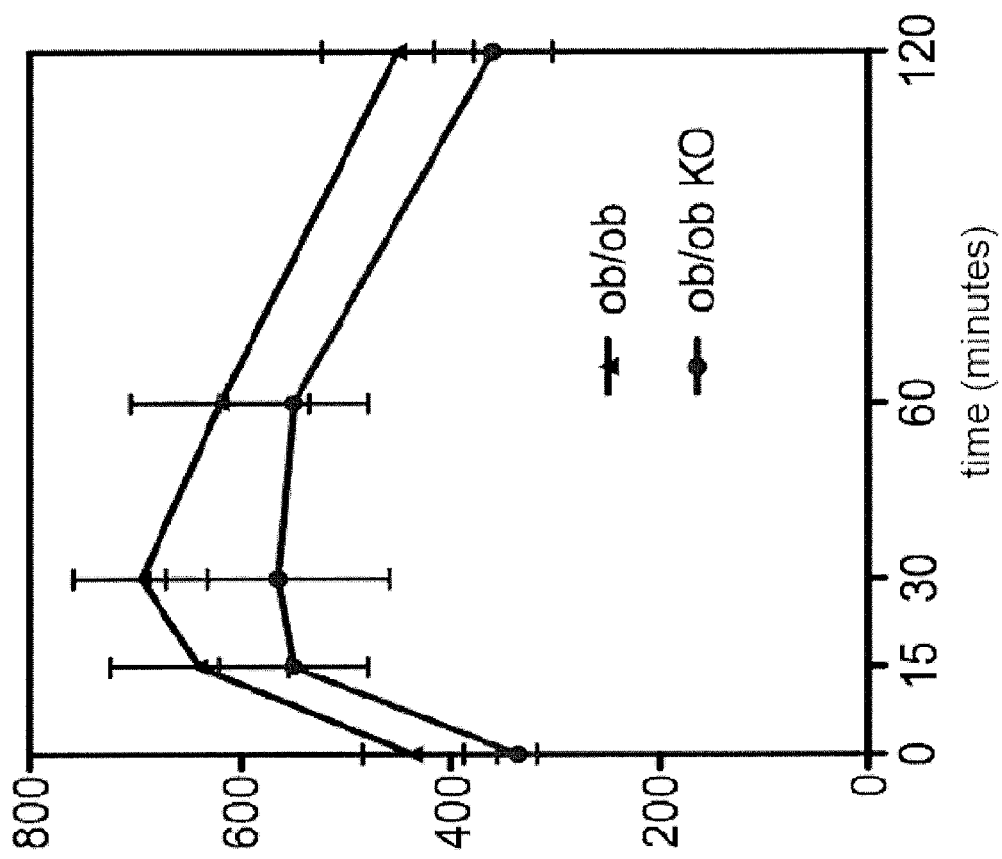
FIG. 12. Obese mice (ob/ob) were crossed with miR-378 knockout animals to obtain obese mice lacking expression of miR-378 (ob/ob KO). Obese mice and the ob/ob KO mice were injected i.p. with 1.5 g/kg glucose after being fasted for 16 hours. Blood glucose levels were assessed at the indicated time points.

MiR-378 Knockout Mice are More Resistant to Weight Gain Induced by High Fat Diet Inhibition of miR-378 using an antisense oligonucleotide produced an improvement in glucose utilization in obese (ob/ob) mice, a model of type 2 diabetes (see Example 4). To further explore the role of miR-378/miR-378* in regulating metabolism, miR-378 knockout mice (see Example 5) were crossed with obese mice and glucose utilization was assessed. Mice were fasted for 16 hours and injected i.p. with 1.5 g/kg glucose. Blood samples were obtained at various intervals after injection to assess blood glucose level. As shown in FIG. 12, the offspring of the miR-378 knockout and ob/ob cross (ob/ob KO) exhibit an improved glucose tolerance as compared to obese (ob/ob) animals.

Figure 13:
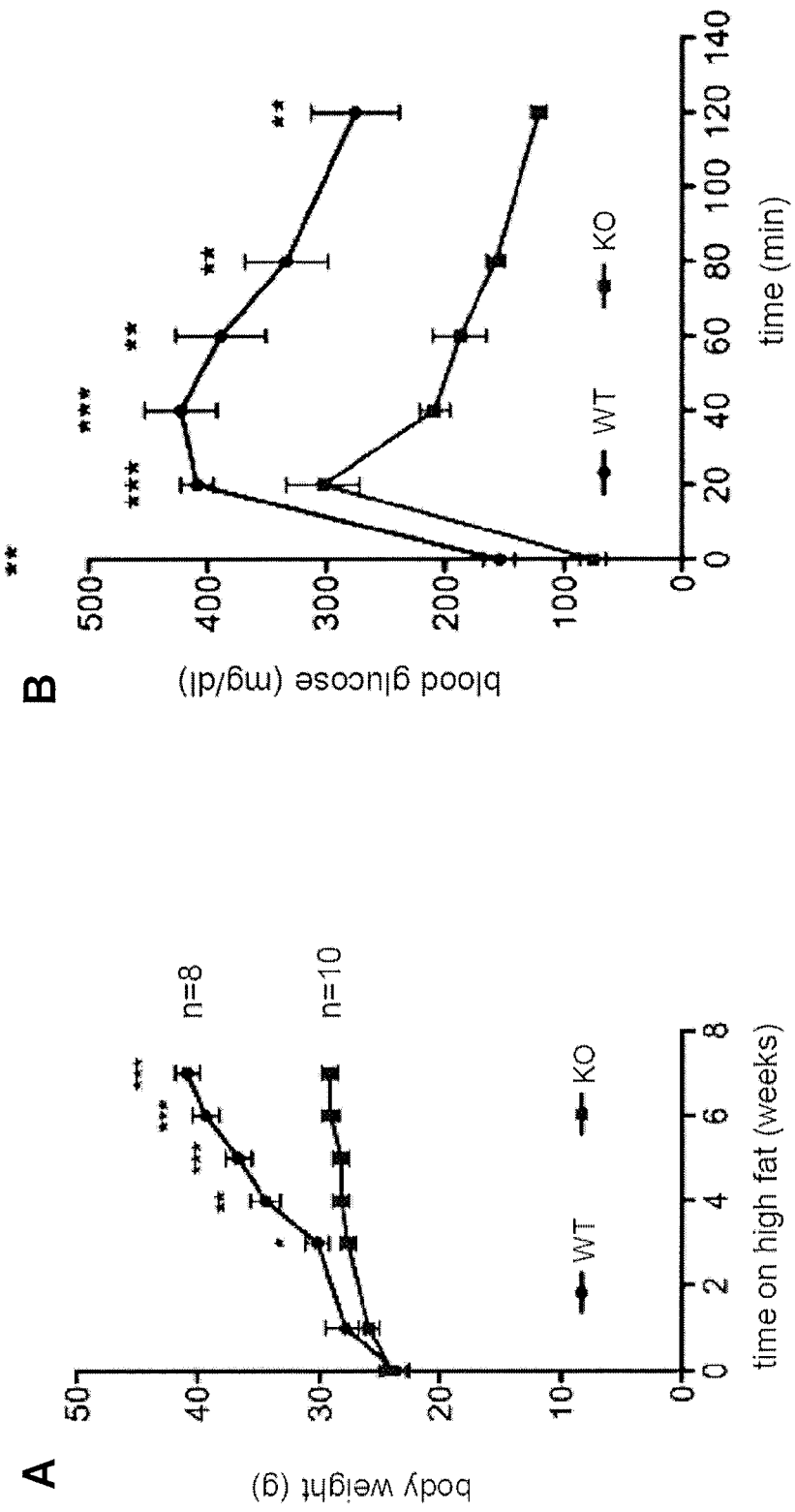
FIG. 13. A. MiR-378 knockout (KO) mice exhibit less body weight gain than wild-type (WT) animals after several weeks on a high fat diet. B. After five weeks on a high fat diet, both miR-378 knockout and wild-type mice were injected i.p. with 1.5 g/kg glucose after being fasted for 16 hours. Blood glucose levels were assessed at the indicated time points.
Figure 14:
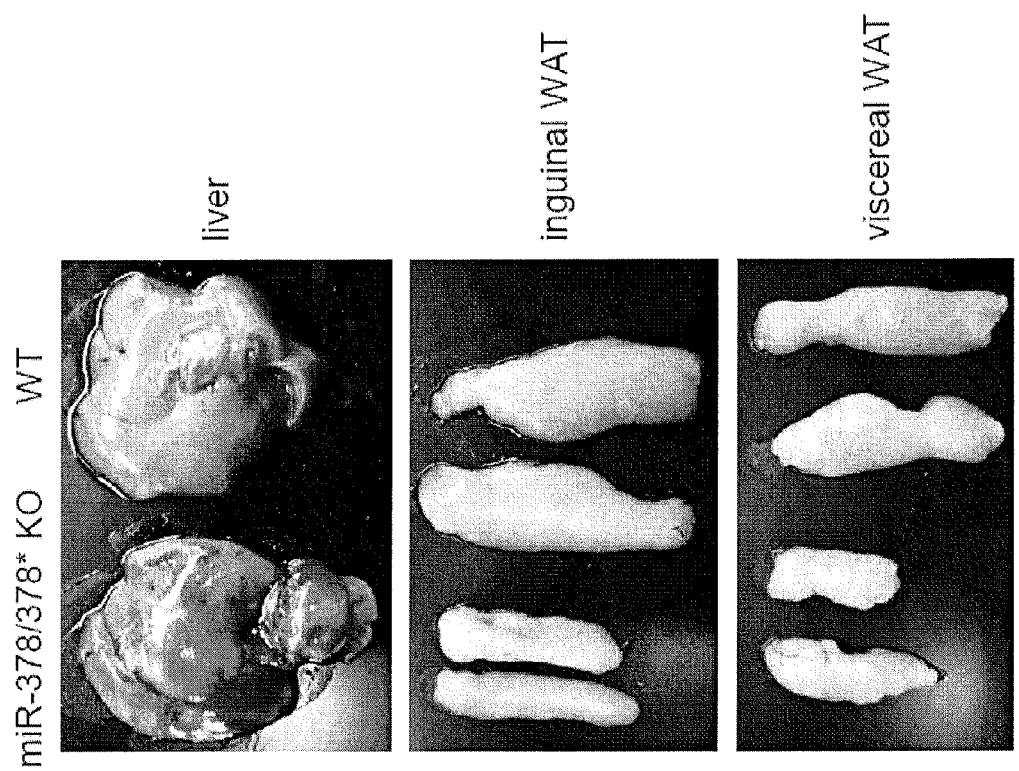
FIG. 14. MiR-378 knockout (KO) mice have reduced fat pads and hepatic lipid accumulation than wild-type (WT) animals after six weeks on a high-fat diet. WAT: white adipose tissue.
Figure 15:
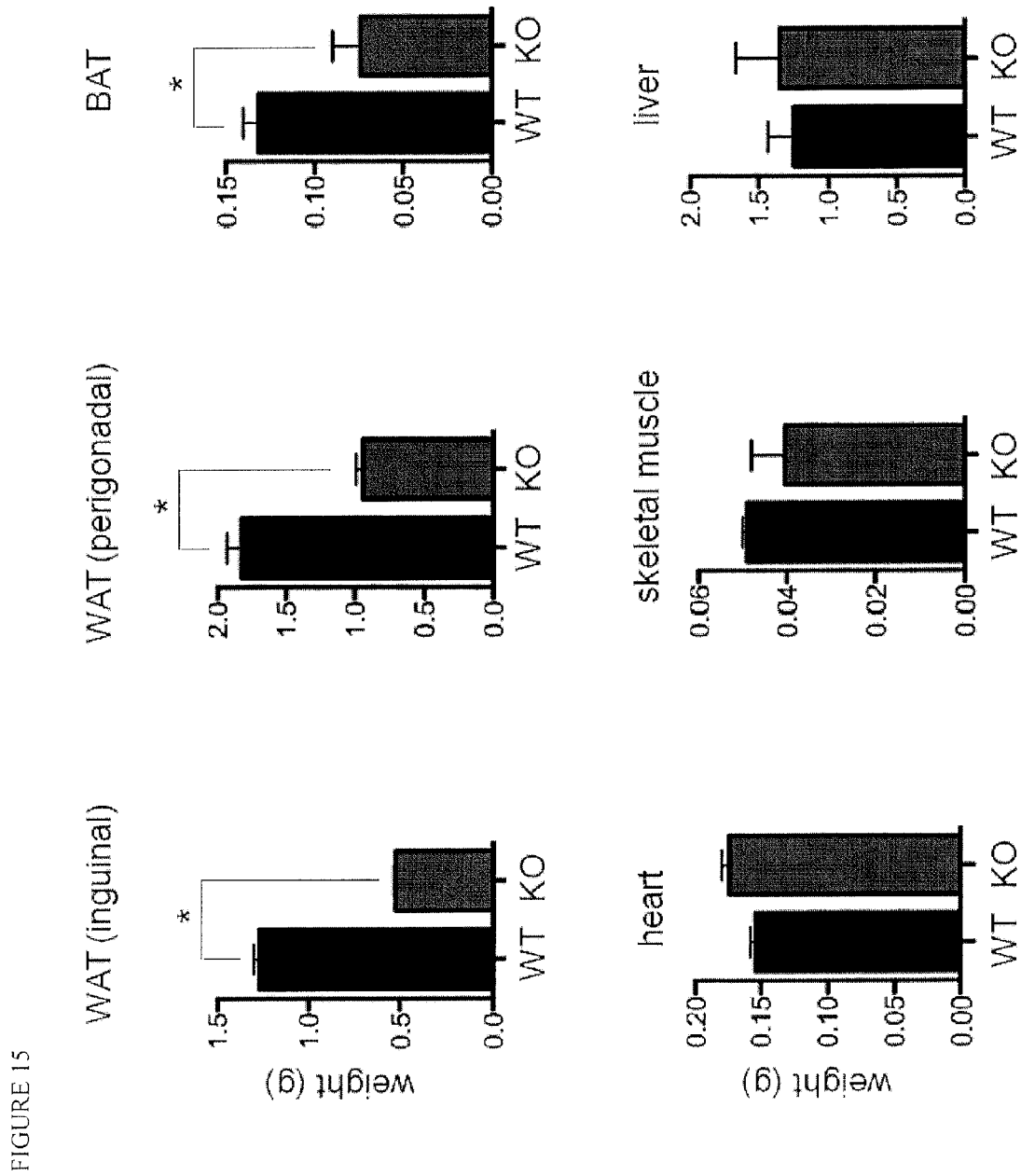
FIG. 15. MiR-378 knockout (KO) mice have reduced fat mass after six weeks on a high-fat diet as compared to wild-type (WT) animals. BAT: brown adipose tissue; WAT: white adipose tissue.
Figure 16:
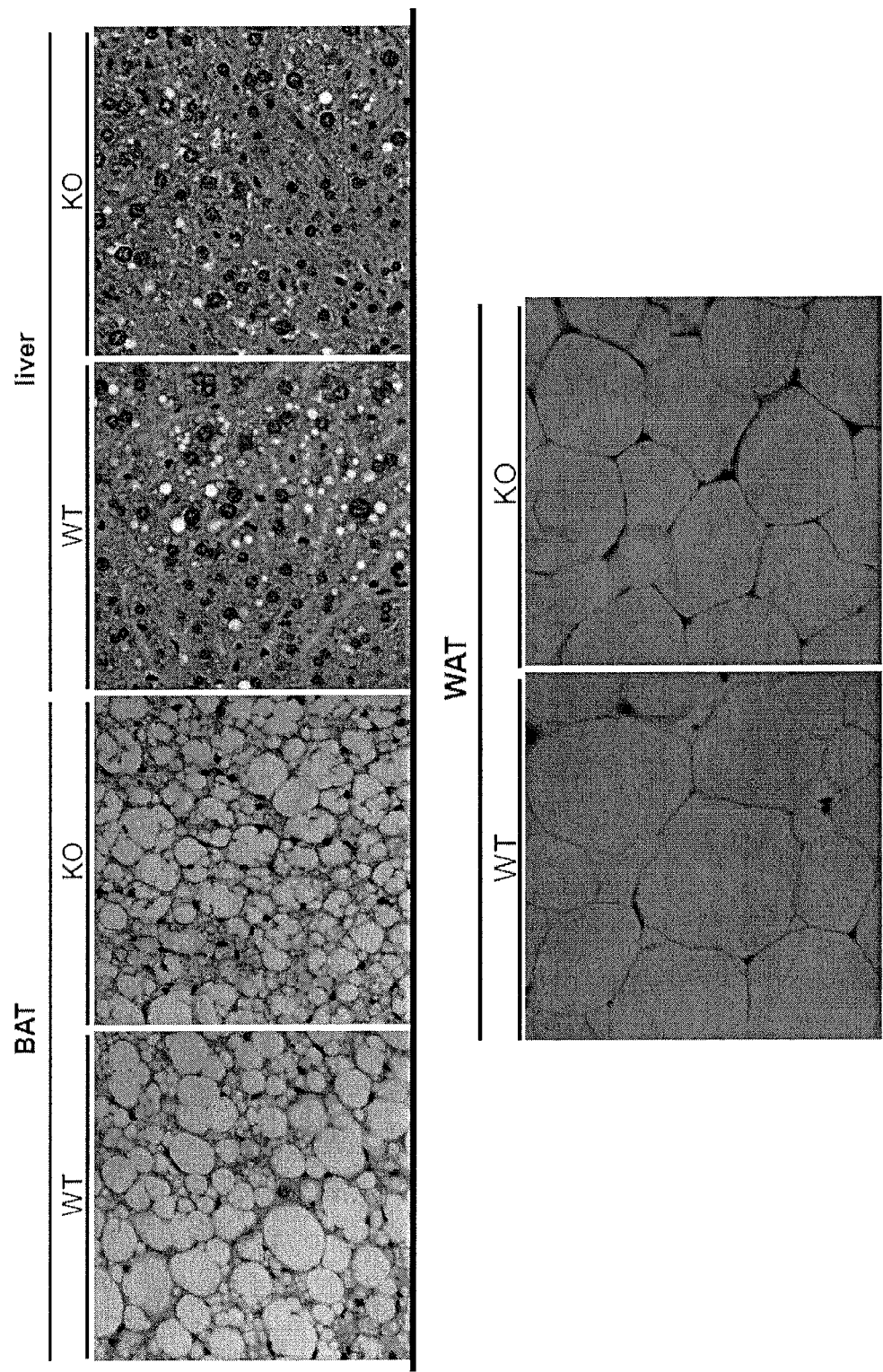
FIG. 16. Histological analysis of white adipose tissue (WAT), brown adipose tissue (BAT), and liver from wild-type (WT) mice and miR-378 knockout (KO) mice following six weeks of a high-fat diet regimen. Magnification: 40×.

To determine whether miR-378/miR-378* plays a role in the development of other forms of obesity, such as that induced by a high-fat diet, miR-378/miR-378* knockout animals and wild-type littermates were put on a high fat diet consisting of 45% kcal fat. The knockout animals gained significantly less body weight than their wild-type counterparts after more than four weeks on the high fat diet (FIG. 13A). In addition, after five weeks on a high fat diet, miR-378/miR-378* knockout animals exhibited enhanced glucose tolerance as compared to wild-type littermates (FIG. 13B). Interestingly, miR-378/miR-378* knockout mice had reduced fat pads and hepatic lipid accumulation after six weeks on a high fat diet as compared to wild-type animals (FIGS. 14-16).

Transgenic mice overexpressing miR-378/miR-378* in heart tissue under the control of an alpha-MHC promoter (see Example 2) had increased body weight as compared to wild-type animals, and also exhibited a greater percentage change in body weight than wild-type animals in response to a high fat diet (FIG. 17).

Western blot analysis of brown adipose tissue isolated from wild-type and miR-378/miR-378* knockout animals following six hours of fasting revealed that AMP-activated protein kinase (AMPK) signaling is enhanced in adipose tissue isolated from the knockout mice as shown by an increase in the phosphorylated form of AMPK (FIG. 18A). AMPK is a central regulator of lipid and glucose metabolism. Activation of AMPK promotes insulin-stimulated glucose uptake and stimulates catabolic processes, such as fatty acid oxidation and glycolysis. Activation of AMPK results in the inhibition of gluconeogenesis, glycogen, lipid and protein synthesis. Therefore, the absence of miR-378/miR-378* in the knockout animals enhances AMPK activation thereby promoting fatty acid oxidation and a reduction in lipid accumulation (FIG. 18B).

Using the miRanda software (available from the Computational Biology Center at Memorial Sloan-Kettering Cancer Center) for the identification of miRNA targets, mediator complex subunit 13 (MED13), also known as thyroid hormone receptor associated protein 1 (THRAP1), was identified as a predicted target for miR-378. The 3' UTR of MED13 contains four putative binding sites for miR-378/miR-378* (FIG. 19A) that are conserved across species (e.g. human, mouse, rat, dog, orangutan, and horse). Examination of MED13 expression in mice overexpressing miR-378/miR-378* in the heart (αMHC Tg) revealed that MED 13 expression is downregulated relative to wild-type animals, while MED 13 expression is upregulated in miR-378/miR-378* knockout animals (KO), suggesting that MED13 is a physiological target of miR-378/miR-378*. See FIG. 19B. To further test whether MED13 is a recognized target for miR-378/miR-378*, the full length 3'-UTR of the MED13 transcript was inserted into a luciferase expression plasmid, which was transfected into COS1 cells. Increasing amounts of CMV-driven miR-378/miR-378* resulted in a dose-dependent decrease in luciferase activity, while comparable amounts of a control miRNA had no effect (FIG. 19C). Mutating the 3'UTR sequence of MED 13 also abrogated miR-378/miR-378*-induced suppression of luciferase activity (FIG. 19C).

Taken together, the results of this series of experiments show that miR-378/miR-378* plays a key role in regulating metabolic processes by influencing AMPK and MED13 signaling. Inhibition of miR-378/miR-378* activity may represent a viable therapeutic approach for treating metabolic disorders, such as obesity and type II diabetes.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating pathologic cardiac hypertrophy, cardiac remodeling, myocardial infarction, or heart failure in a subject in need thereof comprising administering to the subject an inhibitor of miR-378 and/or miR-378*, wherein the inhibitor is an antisense oligonucleotide.

2. The method of claim 1, wherein the expression or activity of miR-378 and/or miR-378* is reduced in the heart cells of the subject following administration of the inhibitor.

3. The method of claim 1, wherein the antisense oligonucleotide comprises a sequence that is at least partially complementary to a mature sequence of miR-378 and/or miR-378*.

4. The method of claim 3, wherein the antisense oligonucleotide comprises a sequence that is substantially complementary to SEQ ID NO: 1 or SEQ ID NO: 2.

5. The method of claim 3, wherein the antisense oligonucleotide comprises at least one sugar and/or backbone modification.

6. The method of claim 5, wherein the sugar modification is a locked nucleic acid.

7. The method of claim 5, wherein the backbone modification is a phosphorothioate linkage.

8. The method of claim 3, wherein the antisense oligonucleotide is about 7 to about 18 nucleotides in length.

9. The method of claim 3, wherein the antisense oligonucleotide has a sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22.

10. The method of claim 1, wherein the subject is human.

11. The method of claim 1, wherein the inhibitor is administered to the subject by an intradermal, subcutaneous, intramuscular, intraperitoneal or intravenous route of administration or by direct injection into cardiac tissue.

12. A method of treating a metabolic disorder in a subject in need thereof comprising administering to the subject an inhibitor of miR-378 and/or miR-378*, wherein the inhibitor is an antisense oligonucleotide, and wherein the expression or activity of miR-378 and/or miR-378* is reduced in the cells of the subject following administration.

13. The method of claim 12, wherein the metabolic disorder is metabolic syndrome, obesity, diabetes mellitus, diabetic nephropathy, insulin resistance, atherosclerosis, a lipid storage disorder, a glycogen storage disease, medium-chain acyl-coenzyme A dehydrogenase deficiency, or aberrant glucose uptake and/or utilization.

14. The method of claim 13, wherein the lipid storage disorder is selected from the group consisting of Niemann-Pick disease, Gaucher's disease, Farber disease, Fabry disease, Wolman disease, and cholesteryl ester storage disease.

15. The method of claim 12, wherein the antisense oligonucleotide comprises a sequence that is substantially complementary to a mature sequence of miR-378 and/or miR-378*.

16. The method of claim 15, wherein the antisense oligonucleotide comprises a sequence that is substantially complementary to SEQ ID NO: 1 or SEQ ID NO: 2.

17. The method of claim 15, wherein the antisense oligonucleotide comprises at least one sugar and/or backbone modification.

18. The method of claim 17, wherein the sugar modification is a locked nucleic acid.

19. The method of claim 17, wherein the backbone modification is a phosphorothioate linkage.

20. The method of claim 15, wherein the antisense oligonucleotide is about 7 to about 18 nucleotides in length.

21. The method of claim 15, wherein the antisense oligonucleotide has a sequence selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, and SEQ ID NO: 22.

22. The method of claim 12, wherein the subject is human.

23. The method of claim 12, wherein the inhibitor is administered to the subject by an intradermal, subcutaneous, intramuscular, intraperitoneal or intravenous route of administration.

24. A method of regulating fatty acid metabolism in a cell comprising contacting the cell with a modulator of miR-378 and/or miR-378* expression or activity, wherein said modulator is an inhibitor of miR-378 and/or miR-378* expression or activity, and wherein said inhibitor is an antisense oligonucleotide.

25. The method of claim 24, wherein fatty acid metabolism is increased in the cell following contact with the miR-378 and/or miR-378* inhibitor as compared to a cell not exposed to the inhibitor.

26. The method of claim 24, wherein the antisense oligonucleotide comprises a sequence that is substantially complementary to a mature sequence of miR-378 and/or miR-378*.

27. The method of claim 26, wherein the antisense oligonucleotide comprises at least one sugar and/or backbone modification.

28. The method of claim 27, wherein the sugar modification is a locked nucleic acid.

29. The method of claim 27, wherein the backbone modification is a phosphorothioate linkage.

30. The method of claim 26, wherein the antisense oligonucleotide is about 7 to about 18 nucleotides in length.

31. The method of claim 24, wherein the cell is a cardiomyocyte, a skeletal muscle cell, a preadipocyte, or an adipocyte.

32. The method of claim 24, wherein the cell is in vitro or in vivo.

* * * * *

SEQUENCE LISTING

```
<160> NUMBER OF SEQ ID NOS: 22

<210> SEQ ID NO 1
<211> LENGTH: 21
<212> TYPE: RNA
<213> ORGANISM: Homo sapiens

<400> SEQUENCE: 1
acuggacuug gagucagaag g                                           21

<210> SEQ ID NO 2
<211> LENGTH: 22
<212> TYPE: RNA
<213> ORGANISM: Homo sapiens

<400> SEQUENCE: 2
cuccugacuc cagguccugu gu                                          22

<210> SEQ ID NO 3
<211> LENGTH: 66
<212> TYPE: RNA
<213> ORGANISM: Homo sapiens

<400> SEQUENCE: 3
agggcuccug acuccagguc cuguguguua ccuagaaaua gcacuggacu uggagucaga    60
aggccu                                                             66

<210> SEQ ID NO 4
<211> LENGTH: 21
<212> TYPE: RNA
```

<213> ORGANISM: Mus musculus

<400> SEQUENCE: 4
acuggacuug gagucagaag g          21

<210> SEQ ID NO 5
<211> LENGTH: 22
<212> TYPE: RNA
<213> ORGANISM: Mus musculus

<400> SEQUENCE: 5
cuccugacuc cagguccugu gu         22

<210> SEQ ID NO 6
<211> LENGTH: 66
<212> TYPE: RNA
<213> ORGANISM: Mus musculus

<400> SEQUENCE: 6
agggcuccug acuccaggguc cuguguguua ccucgaaaua gcacuggacu uggagucaga    60
aggccu       66

<210> SEQ ID NO 7
<211> LENGTH: 21
<212> TYPE: RNA
<213> ORGANISM: Artificial Sequence
<220> FEATURE:
<223> OTHER INFORMATION: miR-378 inhibitor

<400> SEQUENCE: 7
ccuucugacu ccaaguccag u          21

<210> SEQ ID NO 8
<211> LENGTH: 8
<212> TYPE: RNA
<213> ORGANISM: Artificial Sequence
<220> FEATURE:
<223> OTHER INFORMATION: miR-378 inhibitor

<400> SEQUENCE: 8 aguccagu          8

<210> SEQ ID NO 9
<211> LENGTH: 10
<212> TYPE: RNA
<213> ORGANISM: Artificial Sequence
<220> FEATURE:
<223> OTHER INFORMATION: miR-378 inhibitor

<400> SEQUENCE: 9
caaguccagu          10

<210> SEQ ID NO 10
<211> LENGTH: 12
<212> TYPE: RNA
<213> ORGANISM: Artificial Sequence
<220> FEATURE:
<223> OTHER INFORMATION: miR-378 inhibitor

<400> SEQUENCE: 10
uccaagucca gu          12

<210> SEQ ID NO 11
<211> LENGTH: 14
<212> TYPE: RNA

```
<213> ORGANISM: Artificial Sequence
<220> FEATURE:
<223> OTHER INFORMATION: miR-378 inhibitor

<400> SEQUENCE: 11
acuccaaguc cagu                                                           14

<210> SEQ ID NO 12
<211> LENGTH: 16
<212> TYPE: RNA
<213> ORGANISM: Artificial Sequence
<220> FEATURE:
<223> OTHER INFORMATION: miR-378 inhibitor

<400> SEQUENCE: 12
ugacuccaag uccagu                                                         16

<210> SEQ ID NO 13
<211> LENGTH: 16
<212> TYPE: RNA
<213> ORGANISM: Artificial Sequence
<220> FEATURE:
<223> OTHER INFORMATION: miR-378 inhibitor

<400> SEQUENCE: 13
cugacuccaa guccag                                                         16

<210> SEQ ID NO 14
<211> LENGTH: 22
<212> TYPE: RNA
<213> ORGANISM: Artificial Sequence
<220> FEATURE:
<223> OTHER INFORMATION: miR-378* inhibitor

<400> SEQUENCE: 14
acacaggacc uggagucagg ag                                                  22

<210> SEQ ID NO 15
<211> LENGTH: 8
<212> TYPE: RNA
<213> ORGANISM: Artificial Sequence
<220> FEATURE:
<223> OTHER INFORMATION: miR-378* inhibitor

<400> SEQUENCE: 15 gucaggag                                                                   8

<210> SEQ ID NO 16
<211> LENGTH: 10
<212> TYPE: RNA
<213> ORGANISM: Artificial Sequence
<220> FEATURE:
<223> OTHER INFORMATION: miR-378* inhibitor

<400> SEQUENCE: 16
gagucaggag                                                                10

<210> SEQ ID NO 17
<211> LENGTH: 12
<212> TYPE: RNA
<213> ORGANISM: Artificial Sequence
<220> FEATURE:
<223> OTHER INFORMATION: miR-378* inhibitor

<400> SEQUENCE: 17
uggagucagg ag                                                             12
```

```
<210> SEQ ID NO 18
<211> LENGTH: 14
<212> TYPE: RNA
<213> ORGANISM: Artificial Sequence
<220> FEATURE:
<223> OTHER INFORMATION: miR-378* inhibitor

<400> SEQUENCE: 18
ccuggaguca ggag                                                           14

<210> SEQ ID NO 19
<211> LENGTH: 16
<212> TYPE: RNA
<213> ORGANISM: Artificial Sequence
<220> FEATURE:
<223> OTHER INFORMATION: miR-378* inhibitor

<400> SEQUENCE: 19
gaccuggagu caggag                                                         16

<210> SEQ ID NO 20
<211> LENGTH: 16
<212> TYPE: RNA
<213> ORGANISM: Artificial Sequence
<220> FEATURE:
<223> OTHER INFORMATION: miR-378* inhibitor

<400> SEQUENCE: 20
ggaccuggag ucagga                                                         16

<210> SEQ ID NO 21
<211> LENGTH: 15
<212> TYPE: DNA
<213> ORGANISM: Artificial Sequence
<220> FEATURE:
<223> OTHER INFORMATION: miR-378 inhibitor

<400> SEQUENCE: 21
tgactccaag tccag                                                          15

<210> SEQ ID NO 22
<211> LENGTH: 15
<212> TYPE: DNA
<213> ORGANISM: Artificial Sequence
<220> FEATURE:
<223> OTHER INFORMATION: miR-378* inhibitor

<400> SEQUENCE: 22
gacctggagt cagga                                                          15
```